(12) United States Patent
Ernst et al.

(10) Patent No.: US 9,061,982 B2
(45) Date of Patent: Jun. 23, 2015

(54) PROCESS FOR THE PREPARATION OF OXOVINYLIONOL AND ITS O-PROTECTED DERIVATIVES

(71) Applicant: BASF SE, Ludwigshafen (DE)

(72) Inventors: Hansgeorg Ernst, Speyer (DE); Michael Puhl, Hirschberg (DE); Stefan Benson, Heppenheim (DE); Wolfgang Siegel, Limburgerhof (DE)

(73) Assignee: BASF SE (DE)

( * ) Notice: Subject to any disclaimer, the term of this patent is extended or adjusted under 35 U.S.C. 154(b) by 167 days.

(21) Appl. No.: 13/673,278

(22) Filed: Nov. 9, 2012

(65) Prior Publication Data
US 2013/0116473 A1    May 9, 2013

Related U.S. Application Data

(60) Provisional application No. 61/557,440, filed on Nov. 9, 2011.

(51) Int. Cl.
| | | |
|---|---|---|
| C07C 45/34 | (2006.01) | |
| C07C 45/28 | (2006.01) | |
| C07C 409/18 | (2006.01) | |
| C07F 9/54 | (2006.01) | |
| C07C 403/08 | (2006.01) | |
| C07C 407/00 | (2006.01) | |

(52) U.S. Cl.
CPC .............. *C07C 45/28* (2013.01); *C07C 409/18* (2013.01); *C07F 9/5442* (2013.01); *C07C 403/08* (2013.01); *C07C 407/00* (2013.01); *C07C 2101/16* (2013.01)

(58) Field of Classification Search
USPC .......................................... 568/342, 356, 567
See application file for complete search history.

(56) References Cited

U.S. PATENT DOCUMENTS

| | | | |
|---|---|---|---|
| 4,098,827 A | 7/1978 | Rosenberger | |
| 4,585,885 A | 4/1986 | Bernhard et al. | |
| 2009/0093638 A1* | 4/2009 | Doyle et al. | 546/298 |
| 2013/0190528 A1* | 7/2013 | Hage et al. | 562/408 |

FOREIGN PATENT DOCUMENTS

| | | |
|---|---|---|
| CN | 101723769 A | 6/2010 |
| EP | 101597 B1 | 6/1988 |
| EP | 490326 B2 | 6/1998 |
| WO | WO-2007072529 A3 | 11/2007 |
| WO | WO2008/145627 * | 4/2008 ............... C25B 3/02 |
| WO | WO-2008/145627 A1 | 12/2008 |

OTHER PUBLICATIONS

U.S. Appl. No. 61/557,440, filed Sep. 11, 2011, Benson et al.
Rosenberger, Michael, et al., "Canthaxanthin. A New Total Synthesis", J. Org. Chem., vol. 47, (1982), pp. 2130-2134.
Ernst, Hansgeorg, et al., "Recent Advances in Industrial Carotenoid Synthesis", Pure Appl. Chem., vol. 74, No. 11, (2002), pp. 2213-2226.
"Carotenoids", vol. 2: Synthesis, (1996), pp. 281-284.
Rothenberg, G., et al., "Copper-catalyzed Homolytic and Heterolytic Benzylic and Allylic Oxidation Using *tert*-butyl Hydroperoxide", J. Chem. Soc., Perkin Transactions 2, (1998), pp. 2429-2434.

\* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The present invention relates to the preparation of oxovinylionol and its O-protected derivatives of the formula I

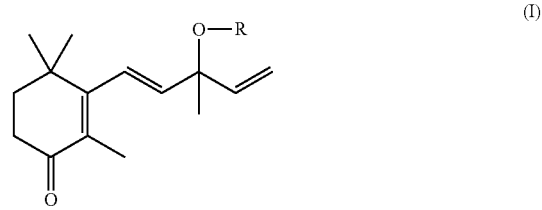

in which R is hydrogen or an OH protecting group, for example a group $Si(R^a)_3$, by reacting a compound of the general formula II

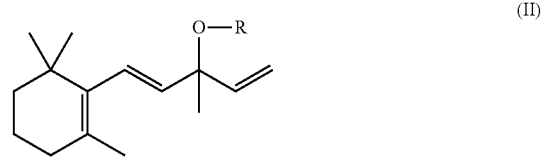

in which R has the meanings given above for formula I, i.e. β-vinyl ionol (formula II, R=hydrogen) or an O-protected derivative thereof (formula II, R=OH protecting group) with an oxidant in the presence of at least one transition metal, where the oxidant comprises at least one oxygen-containing compound which is selected from among hydrogen peroxide and organic hydroperoxides.

18 Claims, No Drawings

PROCESS FOR THE PREPARATION OF OXOVINYLIONOL AND ITS O-PROTECTED DERIVATIVES

CROSS-REFERENCE TO RELATED APPLICATIONS

This application claims the benefit of U.S. Provisional Application No. 61/557,440, filed Nov. 9, 2011, which is incorporated herein by reference.

The present invention relates to the preparation of oxovinylionol and its O-protected derivatives of the formula I

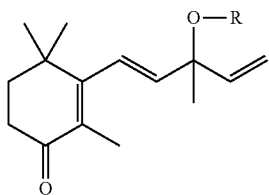

in which R is hydrogen or an OH protecting group, for example a group $Si(R^a)_3$ in which the radicals $R^a$ can be identical or different and independently of one another are $C_1$-$C_4$-alkyl. The invention also relates to the use of compounds of the formula I in the preparation of astaxanthin or canthaxanthin and their precursors, in particular phosphonium salts of the formula IV

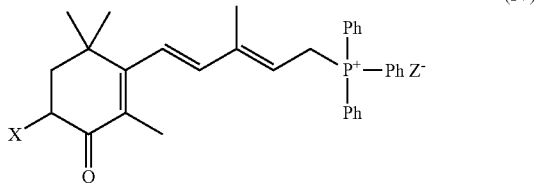

in which X is hydrogen, OH or OR", Ph is phenyl, Z is a halide anion, in particular a bromide anion, and R" is hydrogen or an OH protecting group.

Xanthophyll such as astaxanthin and canthaxanthin are valuable feed additives. For example, astaxanthin is added to fishmeal for farmed salmon in order to obtain the characteristic color of the flesh. Canthaxanthin is used directly for redyeing coley "Seelachs" or admixed to chicken feed so as to make the color of the egg yolk more intense. The central step of the technical synthesis of this compound is the reaction of a phosphonium salt of the formula IV with the C10-dialdehyde (2E,4E,6E)-2,7-dimethyl-octa-2,4,6-trienedial in the sense of a double Wittig olefiniation (see Pure Appl. Chem., 74 (2002) 2213 ff.).

The literature describes various processes for the preparation of phosphonium salts of the formula IV which start with basic petrochemicals. An overview can be found for example in "Carotenoids", volume 2—Synthesis, p. 281-284, Birkhäuser, 1996 and in Pure Appl. Chem., 74 (2002) 2213 ff. These processes involve many steps, which leads to low overall yields and to a high consumption of resources and therefore, ultimately, to high production costs.

WO 2007/072529 describes a process for the preparation of phosphonium salts of the formula IV in which X is OH and Z⁻ is a bromide ion, which process involves 11 steps and starts from readily available β-ionone, comprising the oxidation of β-ionone to give 4-oxo-β-ionone using alkali metal bromides or alkaline earth metal bromides in the presence of iodine or alkali metal iodides or alkaline earth metal iodides in an acidic reaction medium.

EP 101597 describes a process for the preparation of phosphonium salts of the formula IV which departs from oxovinylionol of the formula I (R=hydrogen) and which yields the compound IV in only four steps. However, the disadvantage of said process is that oxovinylionol, in turn, has to date only been obtainable by a multi-step synthesis. Thus, J. Org. Chem., 47 (1982), 2130-2134 and U.S. Pat. No. 4,098,827 describe the preparation of oxovinylionol from readily available α-ionone in a four-step sequence. Again, this way of obtaining the compound IV therefore, ultimately, means a multi-step reaction sequence, which is associated with low overall yields, a high consumption of resources and high production costs.

The present invention is therefore based on the problem of providing a process for the preparation of oxovinylionol (formula I, R=hydrogen) or of its O-protected derivatives (formula I, R=OH protecting group) which permits the preparation of the compounds I in a simple manner and with few steps, starting from readily available starting materials.

Surprisingly, it has been found that this problem is solved by reacting the compound of the formula II, which is readily available,

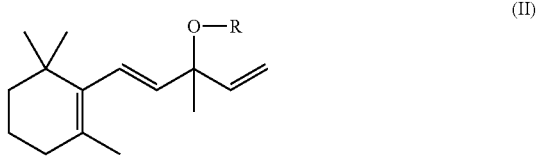

in which R has the meanings specified hereinabove for formula I, i.e. β-vinylionol (formula II, R=hydrogen) or an O-protected derivative thereof (formula II, R=OH protecting group) with an oxidant in the presence of at least one transition metal, where the oxidant comprises at least one oxygen-containing compound selected from among hydrogen peroxide and organic hydroperoxides.

Accordingly, the present invention relates to a process for the preparation of oxovinylionol and its O-protective derivatives of the above-defined formula I, which comprises reacting β-vinylionol or an O-protected derivative thereof of the formula II, in which R has the abovementioned meanings, with an oxidant in the presence of one or more transition metals, where the oxidant comprises at least one oxygen-containing compound selected from among hydrogen peroxide and organic hydroperoxides.

Departing from β-vinylionol, which, being an established vitamin A precursor, is readily available in large amounts, and its O-protected derivatives, the process according to the invention yields oxovinylionol or its O-protected derivatives in good yields in only one reaction step.

In this manner, it is in particular also the availability of the compounds of the formula IV that is simplified, in particular of those compounds of the formula IV in which X is OH and Z⁻ is a bromide ion. Accordingly, the present invention also relates to a process for the preparation of the compounds of the formula IV

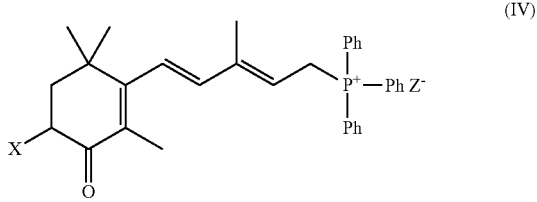

in which X is hydrogen, OH or OR", Ph is phenyl, Z⁻ is a halide anion and R" is hydrogen or an OH protecting group, which comprises the following:
i) providing oxovinylionol or an O-protected derivative thereof of the formula I by the process according to the invention as described here and hereinbelow;
ii) converting oxovinylionol or its O-protected derivative of the formula I in a manner known per se to give a compound of the formula IV, for example by the process of EP 101597, or by the methods described here and hereinbelow.

In formulae I and II, R is hydrogen or an OH protecting group. Suitable OH protecting groups are known to the skilled worker, for example from P. J. Kocienski, Protecting Groups, chapter 2, Georg-Thieme-Verlag, Stuttgart 2000 or P. G. M. Wuts et al. Greene's Protecting groups in Organic Synthesis, 4th edition, John Wiley & Sons, 2006. These include, for example, groups in which the group OR is a component of an ether group, silyl ether group, acetal protecting group, carboxylic ester group or carbonate group. Suitable ether groups OR are, in particular, benzylether groups, tritylether groups, alkylether groups and allylether groups, i.e. R is optionally substituted benzyl, for example benzyl, 4-methoxybenzyl or 3,4-dimethoxybenzyl, triphenylmethyl (trityl), $C_1$-$C_4$-alkyl such as methyl, ethyl or tert-butyl, allyl (2-propenyl) or 2-methoxy-2-propenyl. Suitable silylether groups OR are, in particular, those in which R is a radical of the formula $SiR^aR^bR^c$ in which $R^a$ is $C_1$-$C_4$-alkyl, for example methyl, ethyl, propyl, isopropyl, n-butyl or tert-butyl, $R^b$ and $R^c$ are identical or different and independently of one another are $C_1$-$C_4$-alkyl as defined above, cycloalkyl, for example cyclopentyl or cyclohexyl, or phenyl. Examples of radicals of the formula $SiR^aR^bR^c$ are, in particular, trimethylsilyl, triethylsilyl, triisopropylsilyl, tert-butyldimethylsilyl, tert-butyldiphenylsilyl and diethylisopropyl. Suitable acetal protecting groups are, in particular, those in which the group OR is a component formaldehyde acetal, for example groups in which R is methoxymethyl, 1-methoxy-1-methylethyl, 1-ethoxyethyl, methylthiomethyl, (2-methoxyethoxy)methyl, benzyloxymethyl, β-(trimethylsilyl)ethoxymethyl. An example of an acetal protecting group is, furthermore, the 2-tetrahydropyranyl radical, i.e. R is 2-tetrahydropyranyl. Suitable carboxylic ester groups OR are, in particular, those in which R is acetyl, chloroacetyl, pivaloyl or benzoyl. Suitable carbonate groups OR are, in particular, those in which R is a radical of the formula C(O)—OR$^x$ in which R$^x$ is $C_1$-$C_4$-alkyl, for example tert-butyl, or is allyl, benzyl or fluoren-9-yl methyl.

In formulae I and II, R is preferably hydrogen. If R is a radical other than hydrogen, then it is preferably a radical of the formula $SiR^aR^bR^c$ in which $R^a$, $R^b$ and $R^c$ have the abovementioned meanings and in which $R^b$ and $R^c$ are, in particular, $C_1$-$C_4$-alkyl.

In accordance with the invention, a compound of the formula II in which R has the abovementioned meanings and is, in particular, hydrogen, is reacted with an oxidant in the presence of a transition metal, where the oxidant comprises at least one oxygen-containing compound which is selected among hydrogen peroxide and organic hydroperoxides.

The oxidant preferably comprises at least one organic hydroperoxide. Examples of organic hydroperoxide are alkyl hydroperoxides and aralkyl hydroperoxides, in particular tertiary $C_4$-$C_8$-alkyl hydroperoxides such as tert-butyl hydroperoxide and tert-amyl peroxide, and tertiary phenyl-$C_3$-$C_8$-alkyl hydroperoxides which are optionally substituted on the phenyl ring by 1, 2 or 3 $C_1$-$C_4$-alkyl groups, such as cumene hydroperoxide. Preferred organic hydroperoxides are alkyl hydroperoxides, in particular tertiary $C_4$-$C_8$-alkyl hydroperoxides, specifically tert-butyl hydroperoxide and tert-amyl peroxide, and their mixtures.

The oxygen-containing compound, when used as the oxidant, can be employed alone or in combination with a further oxidant, where the further oxidant is preferably selected from the group of the alkali metal or alkaline-earth-metal halites or hypohalites, in particular from the group of the alkali metal and alkaline-earth metal chlorites and hypochlorites such a sodium chlorite or sodium hypochlorite.

In one embodiment of the invention, the oxygen-containing compound which is selected among hydrogen peroxide and organic hydroperoxides, is employed as the only oxidant. In a preferred embodiment of the invention, at least one organic hydroperoxide selected among alkyl hydroperoxides and aralkyl hydroperoxides, in particular among tertiary $C_4$-$C_8$-alkyl hydroperoxides, such as tert-butyl hydroperoxide and tert-amyl peroxide, and tertiary phenyl $C_3$-$C_8$-alkyl hydroperoxides, such as cumene hydroperoxide, is selected as the only oxidant.

As a rule, the oxidant will be employed in an at least aquimolar amount, i.e. in an amount of at least 1 mol per mole of the compound of the formula II, preferably in an amount of at least 2 mol per mole of the compound of the formula I, for example in an amount of from 1 to 10 mol, in particular from 2 to 7 mol and specifically from 2 to 4 mol per mole of the compound of the formula II. This applies in particular when the oxygen-containing compound selected among hydrogen peroxide and organic hydroperoxides is the only oxidant. If a combination of oxygen-containing compound and further oxidant is employed, these recitations apply to the total amount of the employed equivalents of oxidant, with 1 mol of halite corresponding to 2 mol of the oxygen-containing compound and 1 mol of hypohalite corresponding to 1 mol of the oxygen-containing compound.

In accordance with the invention, a compound of the formula II in which R have the abovementioned meanings and is, in particular, hydrogen is reacted with an oxidant in the presence of at least one transition metal, for example in the presence of one transition metal or in the presence of a combination of 2 or 3 different transition metals. In this context, the at least one transition metal can be employed in elemental form or in the form of a chemical compound, for example in the form of a salt, in the form of an oxide or in the form of a complex compound or a mixture of these. The at least one transition metal is preferably employed in the form of one or more transition metal compounds, in particular in the form of one or more salts and/or one or more complex compounds.

Typically, the at least one transition metal is employed in a total amount of from $5 \times 10^{-6}$ to 0.5 mol, in particular in an amount of from $5 \times 10^{-5}$ to 0.3 mol and specifically in an amount of from $5 \times 10^{-4}$ to 0.3 mol per mole of the compound of the formula II.

Suitable transition metals are namely those from groups 5, 6, 7, 8, 9, 10 or 11 of the Periodic Table (IUPAC nomenclature), for example V, Cr, Mn, Fe, Ru, Co, Rh, Pd, Pt or Cu, in particular those from groups 7, 8, 9, 10 or 11, for example Mn, Fe, Ru, Co, Pt or Cu, and specifically those from groups 7, 9 or 11, and very specifically Cu, Fe, Co or Mn.

If the transition metal is employed in salt form, then suitable counterions are, for example, halide such as chloride, bromide or iodides, pseudohalides such as cyanide, tetrafluoroborate, tetrafluorophosphate, anions of organic monocarboxylic acids, for example $C_1$-$C_{18}$-alkanoate ($=C_1$-$C_{18}$-alkanecarboxylate) which may be chlorinated or fluorinated and/or in which a $CH_2$—$CH_2$ group can be replaced with a $C_3$-$C_6$-cycloalkane-diyl group, such as formate, acetate, propionate, octanoate, the isomers of ethyl hexanoate, naphthenate (=anion of naphthenic acid: mixture of alkylated cycloalkanecarboxylic acids CAS No. 1338-24-5), chloroacetate, dichloroacetate, trichloroacetate, trifluoroacetate, anions of dicarboxylic acids such as oxalate, $C_1$-$C_4$-alkylsulfonate which may be chlorinated or fluorinated, such as methanesulfonate or trifluoromethanesulfonate, arylsulfonate such as phenylsulfonate or toluenesulfonate, sulfate, hydrogen sulfate and triflate.

If the transition metal is employed as a complex compound, then suitable ligands are, for example, acetyl acetonate (acac), pyridine, alkylpyridines, pyrazole, alkylpyrazoles, imidazole, trispyridylmethylamine of the formula A

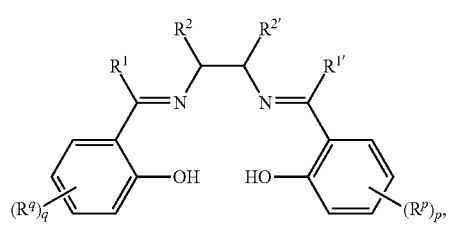

(A)

and ligands of the salen type, which is represented by the following formula B (shown in the protonated, free ligand form), (B)

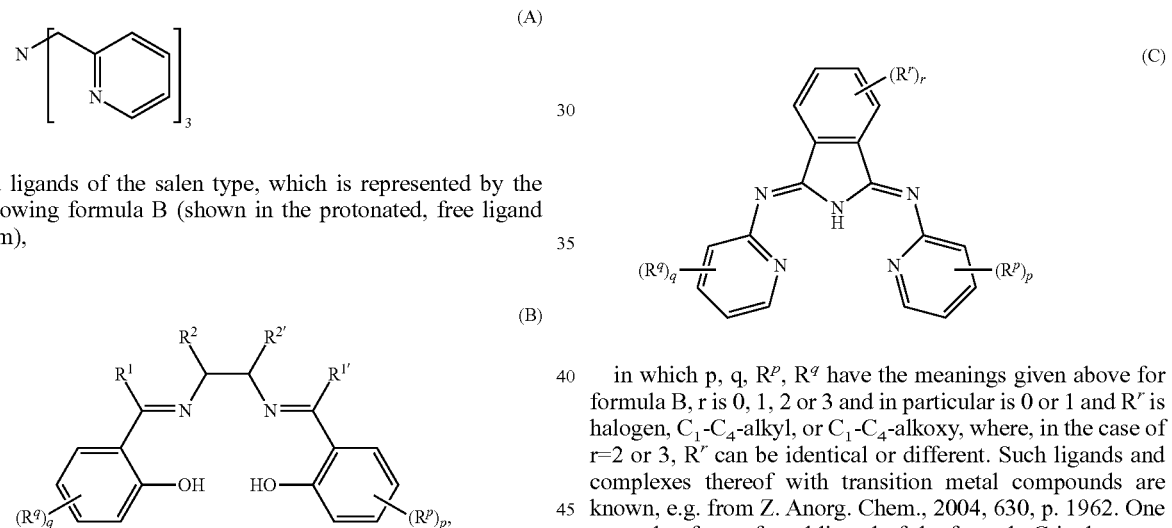

in which $R^1$ and $R^{1'}$ independently of one another are hydrogen or $C_1$-$C_4$-alkyl, $R^2$ and $R^{2'}$ independently of one another are hydrogen or $C_1$-$C_4$-alkyl or together are butane-1,4-diyl; $R^p$, $R^q$ independently of one another are halogen, COOH, $SO_3H$, $C_1$-$C_4$-alkyl, $C_1$-$C_4$-alkoxy or optionally substituted phenyl, and p and q independently of one another are 0, 1, 2, 3 or 4 and in particular 0, 1 or 2, where, in the case of p and/or q=2, 3 or 4, the radicals $R^p$ and $R^q$ can in each case be identical or different. Examples of ligands of the formula B are: N,N'-bis(salicylidene)ethylenediamine (salen-B1 below) and N,N'-bis(salicylidene)cyclohexane-1,2-diamine (salen-B2 below).

Suitable ligands are also compounds which have at least one oxazole group, e.g. oxazole, compounds with a 1,10-phenanthroline group, e.g. 1,10-phenanthroline and substituted 1,10-phenanthrolines, substituted and unsubstituted phthalocyanines, and also compounds with a 2,2-bipyridine group, e.g. 2,2-bipyridine and substituted 2,2-bipyridines. In connection with 1,10-phenanthroline, "optionally substituted" means that one or more hydrogen atoms, for example 1, 2, 3 or 4 hydrogen atoms, of the 1,10-phenanthroline, preferably the hydrogen atoms of the 3, 4, 5, 6, 7 or 8 position, are replaced by substituent groups, the substituents being selected, for example, from among halogen, COOH, $SO_3H$, $C_1$-$C_4$-alkyl, $C_1$-$C_4$-alkoxy, CN and optionally substituted phenyl. In connection with 2,2-bipyridine, "optionally substituted" means that one or more hydrogen atoms, for example 1, 2, 3 or 4 hydrogen atoms, of the 2,2-bipyridine, preferably the hydrogen atoms of the 4, 4', 5 or 5' position, are replaced by substituent groups, the substituents being selected, for example, from among halogen, COOH, $SO_3H$, $C_1$-$C_4$-alkyl, $C_1$-$C_4$-alkoxy, CN and optionally substituted phenyl. In connection with phthalocyanine, "substituted" means that one or more hydrogen atoms, for example 1 to 8 hydrogen atoms, of the phthalocyanine are replaced by substituent groups, the substituents being selected for example from among halogen, COOH, $SO_3H$, $C_1$-$C_4$-alkyl, $C_1$-$C_4$-alkoxy, CN and optionally substituted phenyl. Optionally substituted phenyl means that the phenyl group can carry 1, 2, 3 or 4 substituents which are selected for example from among halogen, COOH, $SO_3H$, $C_1$-$C_4$-alkyl, $C_1$-$C_4$-alkoxy and CN.

Also of suitability are ligands of the general formula C (shown in the protonated, free ligand form)

(C)

in which p, q, $R^p$, $R^q$ have the meanings given above for formula B, r is 0, 1, 2 or 3 and in particular is 0 or 1 and $R^r$ is halogen, $C_1$-$C_4$-alkyl, or $C_1$-$C_4$-alkoxy, where, in the case of r=2 or 3, $R^r$ can be identical or different. Such ligands and complexes thereof with transition metal compounds are known, e.g. from Z. Anorg. Chem., 2004, 630, p. 1962. One example of a preferred ligand of the formula C is the compound C1, in which p, q and r in formula C are 0.

If the transition metals are employed in the form of complex compounds, the complex compound typically has such a number of ligands that the molar ratio, in the complex compound, of all coordination sites of the ligands, which coordinate the metal atom in the complex compound, is typically from 1:1 to 1:6. In the case of monodentate ligands (one coordination site in the ligand), the molar ratio of transition metal to ligand is, therefore, typically from 1:1 to 1:6, in the case of bidentate ligands (two coordination sites in the ligand) typically from 1:1 to 3:1 and in tridentate ligands or ligands with higher denticity, for example tridentate or tetradentate ligands typically from 1:1 to 1.1:1. It is also possible to employ complex compounds which have ligands with different denticities, for example one or more monodentate ligands and one or more bidentate ligands or one or more monodentate ligands and a ligand with higher denticity, for example a tridentate or tetradentate ligand.

The complex compounds of the transition metals can be salt-like, i.e. the negative charge which is optionally introduced by the ligand(s) will not suffice to compensate for the positive charge of the transition metal. In these cases, the complex compounds have one or more of the abovementioned anions as counterions.

The transition metal can also be employed in elemental form. In such a case, it will frequently be employed in supported form, for example on a support selected from among alumina, silica or carbon. The transition metal can also be employed in the form of an oxide or mixture of oxides, for example $Cu_2O$, $Co_2O_3$, or in the form of a mixed oxide, for example as mixed oxides for example aluminum or nickel.

If the transition metal is employed in the form of a salt, a complex compound, an oxide, a mixed oxide or in elemental form, the process according to the invention may also be carried out in the presence of one or more of the ligands mentioned in connection with the transition metal complex compounds. If the ligand is liquid, for example in the case of pyridine, the reaction may be carried out in the ligand, which acts as the solvent or diluent.

In a preferred embodiment, the reaction of the compound of the formula II with the oxidant takes place in the presence of at least one ligand which is suitable for forming one or more coordination bonds with the transition metal. For this, the ligand can be used in the form of the transition metal complex compound which already comprises the ligand, or added to the reaction mixture separately from the transition metal, in which case presumably a complex compound is formed under the reaction conditions which comprises the transition metal and the ligand.

For this purpose, preference is given in particular to those ligands which comprise at least one nitrogen atom. Examples of ligands of this type are pyridine, alkylpyridines, pyrazole, alkylpyrazoles, imidazole, trispyridylmethyamines of the formula A, ligands of the salen type of the formula B, ligands of the formula C, compounds which have at least one oxazole group, e.g. oxazole, compounds with a 1,10-phenanthroline group, e.g. 1,10-phenanthroline and substituted 1,10-phenanthrolines, substituted and unsubstituted phthalocyanines, and also compounds with a 2,2-bipyridine group. For this purpose, particular preference is given to those ligands in which the at least one nitrogen atom is present in the form of an oxazole, 2,2-bipyridine and 1,10-phenanthroline group.

If the reaction of the compound of the formula II with the oxidant in the presence of at least one ligand which is suitable for forming one or more coordination bonds with the transition metal, in particular in the presence of at least one ligand which comprises at least one nitrogen atom, and specifically at least one ligand from the group, pyridine, bipyridine compounds, phenanthroline compounds, oxazole compounds and ligands of the general formulae A, B and C, very specifically from the group of the ligands which have an oxazole, 2,2-bipyridine and 1,10-phenanthroline group, the molar ratio of metal to ligand is preferably in the range from 0.5:1 to 2:1.

In particular, the transition metal is used in the form of at least one compound which are selected from among the halides, acetylacetonates, oxalates and salts of organic monocarboxylic acids, such as naphthenates or $C_2$-$C_{18}$-alkanoates, of copper, of cobalt or of manganese and the N,N-salicyliminoethane complexes of copper, of cobalt or of manganese, and which are selected specifically from among CuCl, $CuCl_2$, CuI, $CoCl_2$, Cu(II) oxalate, Co(II) salts of organic monocarboxylic acids (e.g. of napthenates or $C_1$-$C_{18}$-alkanoates), such as $Co(formate)_2$, $Co(acetate)_2$, $Co(2\text{-ethylhexanoate})_2$ or $Co(naphthenate)_2$, Co(II) oxalate, $Co(acac)_2$, $Co(acac)_3$, Co(salen), Co(salen)Cl, Mn(salen) and Mn(salen)Cl, and $Mn(acac)_2$, where acac is acetylacetonate and salen is the N,N'-bis(salicylidene)ethylenediamino ligand B1. The aforementioned transition metal compounds here can be used as they are or in the presence of further ligands, specifically in the presence of at least one ligand from the group of bipyridine compounds, phenanthroline compounds and oxazole compounds and very specifically in the presence of a phenanthroline ligand. In this very specific embodiment, the molar ratio of metal to ligand is preferably in the range from 0.5:1 to 2:1.

In a specific embodiment, at least one transition metal compound is used which is selected from among compounds of cobalt, in particular from among acetylacetonates, naphthenates and $C_1$-$C_{18}$-alkanoates of cobalt and N,N-salicyliminoethane complexes of cobalt, e.g. cobalt bisacetylacetonate, cobalt trisacetylacetonate, cobalt(II) 2-ethylhexanoate, cobalt(II) acetate, cobalt(II) oxalate, cobalt(II) naphthenate, cobalt(II) salicyliminoethane, chlorocobalt(III) salicyliminoethane. Preferably, in this specific embodiment, the reaction is carried out in the presence of at least one further ligand, in particular in the presence of at least one ligand from the group of bipyridine compounds, phenanthroline compounds and oxazole compounds and very specifically in the presence of a phenanthroline ligand. In this very specific embodiment, the molar ratio of metal to ligand is preferably in the range from 0.5:1 to 2:1.

In a further specific embodiment of the process according to the invention, the transition metal employed is at least one salt of copper, of cobalt, of iron or of manganese or a mixture of these, which salt is selected in particular among the halides, acetylacetonates (acac), oxalates, salts of organic monocarboxylic acids such as naphthenates or $C_2$-$C_{18}$-alkanoates of copper, of cobalt or manganese and the complexes of N,N-salicyliminoethane (B-1) with copper, cobalt or manganese and their mixtures. In a specific embodiment, at least one salt selected from among CuCl, CuI, $CuCl_2$, $CoCl_2$ and their mixtures is employed. In another specific embodiment of the process according to the invention, the transition metal employed is at least one acetylacetonate, oxalate, naphthenate or $C_2$-$C_{18}$-alkanoate of cobalt or of manganese or a complex of cobalt or of manganese with N,N-salicyliminoethane (ligand (B1), for example cobalt bisacetylacetonate, cobalt (II) 2-ethylhexanoate, cobalt(III) trisacetylacetonate, cobalt (II) oxalate, cobalt(II) acetate, cobalt(II) naphthenate, cobalt (II) salicyliminoethane, chlorocobalt(III) salicyliminoethane, manganese(II) salicyliminoethane, chloromanganese(III) salicyliminoethane, manganese trisacetylacetonate or a manganese bisacetylacetonate alkanoate. In a further specific embodiment of the process according to the invention, the transition metal employed is at least one acetylacetonate, naphthenate, $C_2$-$C_{18}$-alkanoate or an N,N-salicylimino-ethane complex of copper, for example copper(II) acetate.

In a very specific embodiment of the process according to the invention, the transition metal employed is at least one salt of copper, of manganese, of copper or of cobalt, in particular at least one halide of copper or of cobalt, specifically CuCl, $CoCl_2$ or CuI, or at least one acetylacetonate, $C_2$-$C_{18}$-alkanoate, oxalate, naphthenate or N,N-salicyl-iminoethane complex of copper, of cobalt or of manganese, for example cobalt bisacetylacetonate, cobalt(II) 2-ethylhexanoate, copper(II) acetate, cobalt(III) trisacetylacetonate, cobalt(II) oxalate, cobalt(II) acetate, cobalt(II) naphthenate, cobalt(II) salicyliminoethane, chlorocobalt(III) salicyliminoethane, manganese(II) salicyliminoethane, chloromanganese(III) salicyliminoethane, manganese bisacetylacetonate alkanoate, and the reaction is carried out in the presence of one or more of the ligands mentioned in connection with the transition metal complex compounds, in particular in the presence of at least one ligand which comprises at least one nitrogen atom, and especially at least one ligand from the group of pyridine, bipyridine compounds, phenanthroline compounds, oxazole compounds and ligands of the general formulae A, B and C, very especially from the group of the ligands which have an oxazole, 2,2-bipyridine and 1,10-phenanthroline group, and especially in the presence of pyridine or in the presence of phenanthroline, bipyridine or oxazole.

In a further very specific embodiment, at least one acetylacetonate, naphthenate, oxalate or $C_2$-$C_1$ α-alkanoate of copper, of cobalt or of manganese or an N,N-salicyl-iminoethane complex of copper, of cobalt or of manganese is employed, for example cobalt bisacetylacetonate, cobalt(II) 2-ethylhexanoate, cobalt trisacetylacetonate, copper(II) acetate, cobalt (II) oxalate, cobalt(II) acetate, cobalt(II) naphthenate, cobalt (II) salicyliminoethane, chlorocobalt(III) salicyliminoethane, manganese(II) salicyliminoethane, chloromanganese(III) salicyliminoethane, manganese trisacetylacetonate or a manganese bisacetylacetonate alkanoate, and the reaction is carried out in an organic solvent or solvent mixture selected from among $C_1$-$C_4$-alkyl esters of acetic acid, for example ethyl acetate, acetonitrile, dimethylformamide, N-methylpyrrolidone or toluene, their mixtures and mixtures of one or more of these solvents with pyridine. The amount of pyridine in these mixtures is typically from 1 to 10 mols per mole of transition metal.

In a further very specific embodiment, at least one transition metal compound is used which is selected from among acetylacetonates, naphthenates, $C_2$-$C_{18}$-alkanoates of copper, of cobalt or of manganese and N,N-salicyliminoethane complexes of copper, of cobalt or of manganese, e.g. cobalt bisacetylacetonate, cobalt trisacetylacetonate, copper(II) acetate, cobalt(II) oxalate, cobalt(II) acetate, cobalt(II) naphthenate, cobalt(II) 2-ethylhexanoate, cobalt(II) salicyliminoethane, chlorocobalt(III) salicyliminoethane, manganese(II) salicyliminoethane, chloromanganese(III) salicyliminoethane, manganese trisacetylacetonate or a manganese bisacetylacetonate-alkanoate, and the reaction is carried out in an organic solvent or solvent mixture which from among $C_1$-$C_4$-alkylesters of acetic acid, e.g. ethyl acetate, acetonitrile, dimethylformamide, N-methylpyrrolidone or toluene, and in the presence of at least one further ligand, in particular in the presence of at least one ligand which comprises at least one nitrogen atom, and specifically at least one ligand from the group of bipyridine compounds, phenanthroline compounds and oxazole compounds and very specifically in the presence of a phenanthroline ligand. In this very specific embodiment, the molar ratio of metal to ligand is preferably in the range from 0.5:1 to 2:1.

In a further very specific embodiment, at least one transition metal compound is used which is selected from among acetylacetonates, naphthenates, $C_2$-$C_{18}$-alkanoates of copper, of cobalt or of manganese and N,N-salicyliminoethane complexes of copper, of cobalt or of manganese, e.g. cobalt bisacetylacetonate, cobalt trisacetylacetonate, copper(II) acetate, cobalt(II) oxalate, cobalt(II) acetate, cobalt(II) 2-ethylhexanoate, cobalt(II) naphthenate, cobalt(II) salicylimino-ethane, chlorocobalt(III) salicylimino-ethane, manganese(II) salicyliminoethane, chloromanganese(III) salicyliminoethane, manganese trisacetylacetonate or a manganese bisacetylacetonate-alkanoate, and the reaction is carried out in the absence of an organic solvent. In this embodiment, the reaction can be carried out in the absence of further ligands and in particular in the presence of at least one further ligand, in particular in the presence of at least one ligand which comprises at least one nitrogen atom, and specifically in the presence of at least one ligand from the group of bipyridine compounds, phenanthroline compounds and oxazole compounds and very specifically in the presence of a phenanthroline ligand. In this very specific embodiment, the molar ratio of metal to ligand, if used, is preferably in the range from 0.5:1 to 2:1.

In a further very specific embodiment, at least one transition metal compound is used which is selected from among compounds of cobalt, in particular from among acetylacetonates, naphthenates and $C_2$-$C_{18}$-alkanoates of cobalt and N,N-salicyl-iminoethane complexes of cobalt, e.g. cobalt bisacetylacetonate, cobalt trisacetyl-acetonate, cobalt(II) 2-ethylhexanoate, cobalt(II) acetate, cobalt(II) oxalate, cobalt(II) naphthenate, cobalt(II) salicyliminoethane, chlorocobalt(III) salicyliminoethane, and the reaction is carried out in an organic solvent or solvent mixture which from among $C_1$-$C_4$-alkyl esters of acetic acid, e.g. ethyl acetate, acetonitrile, dimethylformamide, N-methylpyrrolidone or toluene, and in the presence of at least one further ligand, in particular in the presence of at least one ligand from the group of the phenanthroline compounds. In this very specific embodiment, the molar ratio of metal to phenanthroline compound is preferably in the range from 0.5:1 to 2:1.

In a further very specific embodiment, at least one transition metal compound is used which is selected from among acetylacetonates, naphthenates, $C_2$-$C_{18}$-alkanoates of cobalt and N,N-salicyliminoethane complexes of cobalt, e.g. cobalt bisacetylacetonate, cobalt trisacetylacetonate, cobalt(II) oxalate, cobalt(II) 2-ethylhexanoate, cobalt(II) acetate, cobalt(II) naphthenate, cobalt(II) salicyliminoethane, chlorocobalt(III) salicyliminoethane, and the reaction is carried out in the presence of at least one further ligand, in particular in the presence of at least one ligand from the group of the phenanthroline compounds and in the absence of solvents. In this very specific embodiment, the molar ratio of metal to phenanthroline compound is preferably in the range from 0.5:1 to 2:1.

The transition metal is typically employed in an amount of from $5 \times 10^{-6}$ to 0.5 mol, in particular in an amount of from $5 \times 10^{-6}$ to 0.3 mol and specifically in an amount of from $5 \times 10^{-4}$ to 0.3 mol per mole of the compound of the formula II. In the case of copper, cobalt or manganese, the transition metal is, as a rule, employed in an amount of from $5 \times 10^{-6}$ to 0.5 mol, in particular in an amount of from $10^{-4}$ to 0.3 mol per mole of the compound of the formula II.

The compound of the formula II is typically reacted with the oxidant in a solvent or diluent. Suitable solvents/diluents are, in principle, all organic solvents which are inert under reaction conditions, and water. Suitable inert organic solvents are halogenated solvents such as dichloromethane (DCM), chloroform, dichloroethane (DCE) and chlorobenzene, furthermore polar aprotic solvents such as pyridine, acetonitrile, N-methylpyrrolidone, dimethylformamide or the $C_1$-$C_4$-alkyl esters of acetic acid, and aliphatic and cycloaliphatic hydrocarbons such as hexane, heptane, octane and their isomer mixtures, cyclohexane, methylcyclohexane and cycloheptane, and aromatic hydrocarbons such as benzene, toluene, xylenes, furthermore mixtures of the abovementioned organic solvents, and mixtures of these with water. Other suitable solvents/diluents are ionic liquids such as (di)alkylimidazolium salts, for example their chlorides, bromides, trifluoroacetates, sulfonates, sulfate, hydrogen sulfates, metosulfates, carbonates, hydrogencarbonates and triflate. Another advantageous way of carrying out the reaction is in the 2-phase system water and organic solvent. When doing so, it is also possible to add phase-transfer catalysts such as, for example, tetraalkylammonium salts or trialkylbenzylammonium salts, for example tetra-$C_1$-$C_4$-alkylammonium halides, tri-$C_1$-$C_4$-alkylbenzylammonium halides or tri-$C_1$-$C_4$-alkyl-$C_6$-$C_{20}$-alkylammonium halides.

In a preferred embodiment of the invention, the solvent or diluent comprises at least one organic solvent selected from among pyridine, acetonitrile and ethyl acetate. In a further preferred embodiment of the invention, the solvent or diluent comprises at least one organic solvent selected from among methylpyrrolidone and dimethylformamide.

If the compound II is reacted with the oxidant in a solvent or diluent, the concentration of compound II will typically be selected in the range of from 5 to 70% by weight, frequently from 5 to 60% by weight and specifically from 5 to 50% by weight, based on the total weight of the reaction mixture.

The reaction temperatures required for reacting the compound of the formula II with the oxidant can be determined by a person skilled in the art using routine measures; they are typically in the range of from 0 to 100° C., frequently in the range of from 15 to 100° C., preferably in the range of from 20 to 100° C. and in particular in the range of from 30 to 95° C. The reaction pressure has no, or only a minor, effect on the reaction and is therefore in the range of from 700 to 1500 mbar, with lower or higher pressures also being possible. The reaction may be carried out in an inert atmosphere, for example on the inert gas such as nitrogen or argon. The reaction times required for reacting the compound of the formula II with the oxidant can be determined by a person skilled in the art using routine measures; they are typically in the range of from 10 min to 48 h, in particular in the range of from 30 min to 24 h.

To carry out the reaction, the compound of the formula II will typically be brought into contact with the oxidant and the at least one transition metal, preferably the at least one transition metal compound, in a suitable reaction vessel. To this end, it is possible for example to first introduce the compound of the formula II into a suitable reaction vessel and to add the oxidant and the at least one transition metal thereto. It is also possible to introduce the compound of the formula II together with the at least one transition metal into a suitable reaction vessel and to add the oxidant thereto. It is also possible to introduce the compound of the formula II together with the at least one transition metal and the oxidant into a suitable reaction vessel and then to heat the mixture to the reaction temperature.

The oxidant can be employed in pure form or as a solution in water or an inert organic solvent or mixtures of inert organic solvents or mixtures of water and inert organic solvents. Substances which may be mentioned are, in particular, $C_6$-$C_{20}$-alkanes, acetonitrile, $C_1$-$C_4$-alkyl esters of acetic acid, such as ethyl acetate, or pyridine, and mixtures of these. The concentration of peroxide is then preferably in the range from 10 to 90% by weight, in particular in the range from 30 to 70% by weight. According to one preferred embodiment, an alkyl peroxide in the form of an aqueous solution is used as oxidant. The concentration of alkyl peroxide in the aqueous solution is then preferably in the range from 10 to 90% by weight, in particular in the range from 30 to 70% by weight. The alkyl peroxide can additionally be diluted with fractions of one or more of the organic solvents suitable for the reaction and specified above. Preference is given to using 0.1 to 10 mol, particularly preferably 1 to 5 mol, of solvent per mole of compound of the formula II. A second solvent can also be used here. The alkyl peroxide can, however, also be used dissolved in an organic solvent, in particular in aliphatic $C_6$-$C_{12}$-hydrocarbons (branched or unbranched). Preferred $C_6$-$C_{12}$-hydro-carbons are decane or undecane and mixtures thereof. The alkyl peroxide can, however, also be used in the form of a solution in dialkyl peroxide. One example to be mentioned here is Luperox® as commercially available form.

The oxidant can be introduced as initial charge in one portion or be added at the start of the reaction in one portion. Some or all of the oxidant can also be added in the course of the reaction.

Naturally, the at least one transition metal may be added at different points in time, for example some will be added at the beginning of the reaction or will be introduced initially in the reaction mixture, and the remaining amount of transition metal will be added in one or more portions during the course of the reaction. The at least one further transition metal which is added in the course of the reaction can be identical to or different from the transition metal added at the beginning of the reaction or introduced in the reaction mixture.

In a specific embodiment of the invention, the reaction of the compound of the formula II is carried out such that firstly the compound of the formula III described below is prepared, this is optionally isolated and then the compound of the formula III is decomposed to give the compound of the formula I.

The preparation of the compound of the formula I from the compound II via the intermediate III can take place for example by firstly adding only some of the at least one transition metal to the reaction vessel at the start of the reaction, as a result of which the compound of the formula III is primarily formed. The compound of the formula III is then decomposed, for example by heating, by adding further transition metal, by adding a base, in particular a nitrogen base, specifically with the addition of a secondary or tertiary amine or by combining one or more of these measures.

The preparation of the compound of the formula I via the intermediate III can also take place for example by reacting the reaction of the compound of the formula II with the oxidant in the presence of the transition metal and optionally one or more of the ligands described above at low temperatures, primarily forming the compound of the formula III, which is then decomposed to the compound of the formula I, for example by heating, by adding a base, in particular a nitrogen base, specifically with the addition of a secondary or tertiary amine or by combining one or more of these measures. Preferred temperatures for the conversion of the compound II to the compound III are in the range from 0 to 100° C., in particular in the range from 10 to 60° C.

According to one embodiment, the decomposition of the compound III to the compound I takes place thermally. For this, the compound of the formula III or the reaction mixture from the reaction of the compound II with the oxidant is heated to temperatures of usually at least 40° C., often at least 50° C. and in particular at least 60° C., e.g. 40 to 100° C., in particular 50 to 95° C. and specifically 60 to 90° C. Optionally, low-boiling constituents can be removed from the reaction mixture by distillation beforehand. The thermal decomposition is preferably carried out here until at least 90%, in particular the total amount of the compound of the formula III, has reacted. The time required for this naturally depends on the type of reaction mixture and the temperature and is typically in the range from 2 to 24 h.

According to another embodiment, the decomposition of the compound III to the compound I takes place by treatment with base, where the reaction mixture can be enriched beforehand with regard to the compound III, e.g. through distillative removal of low-boiling constituents. For the treatment of the compound III with the base, the compound of the formula III or the reaction mixture from the reaction of the compound II is admixed with the base, where the base can be added to the compound of the formula III or to the reaction mixture from the reaction of the compound II, or the compound of the formula III or the reaction mixture from the reaction of the compound II with the oxidant is added to the base. The amount of base is typically in the range from 1 to 10 mol, in particular 1 to 5 mol and specifically 1 to 3 mol per mole of compound of the formula III. Suitable bases are nitrogen bases, in particular secondary or tertiary mono- or diamines, in particular $C_1$-$C_{10}$-trialkylamines, tetra-$C_1$-$C_4$-alkyl-diaminoalkanes and saturated 5-7-membered nitrogen heterocycles, which optionally carry a $C_1$-$C_{10}$-alkyl group on the nitrogen atom, and oxo bases, in particular alkali metal carbonates, hydrogencarbonates, hydroxides and $C_1$-$C_{10}$-alcoholates, in particular the corresponding sodium, potassium and lithium compounds, alkaline earth metal hydroxides and $C_1$-$C_{10}$-alcoholates, in particular the corresponding calcium and magnesium compounds, and also ammonium carbonate, ammonium hydrogen-carbonates and ammonium hydroxide. Examples of nitrogen bases are in particular morpholine, piperidine, N-methylpiperidine, triethylamine, diisopropylethylamine and tripropylamine, and also N,N,N',N'-tetramethyl-1,2-diaminoethane. Examples of oxo bases are in particular sodium methanolate, potassium methanolate, potassium tert-butanolate, lithium hydroxide, calcium hydroxide and magnesium hydroxide. The reaction time for the decomposition of III initiated by bases is typically in the range from 1 h to 24 h. The reaction temperature for the decomposition of III initiated by bases is typically in the range from 25° C. to 100° C.

In a further specific embodiment, some of the at least one transition metal is placed into the reaction vessel at the beginning of the reaction or introduced therein. This results first in the formation of intermediate of the formula III (see hereinbelow), which is then converted into the compound I upon addition of further transition metal, which may be identical to or different from the transition metal which has been added first. For example, the oxidation of II which gives the compound I may be carried out in such a way that the compound II is first converted with the oxidant in the presence of at least one transition metal into the compound III described below, and the latter is reacted further by addition of at least one of the transition metals specified herein as being preferred, which is preferably copper, cobalt or manganese and specifically copper, preferably in the form of a transition metal compound, in particular in the form of a complex or a salt, in particular copper in the form of a salt, such as CuCl or CuI, to give the compound I. Specifically, the further transition metal, which is preferably copper, is added in the form of a solution of a suitable transition metal compound, in particular in the form of a solution of a suitable transition metal salt such as CuCl or CuI in an organic solvent or solvent mixture which contains pyridine. The amount of further transition metal is approximately $5 \times 10^{-4}$ to 0.05 mol, in particular in the range of from $10^{-3}$ to 0.03 mol per mole of the compound II.

It is preferred to ensure that the reaction mixture is mixed during the reaction, for example by stirring or by recirculating.

The reaction yields the desired compound of the formula I in good yields. It generates primarily the compound of the formula III, which then becomes converted into the compound I, preferably with heating and/or the addition of further transition metal and/or by addition of a base, in particular a nitrogen base, especially with addition of a secondary or tertiary amine or an oxo base.

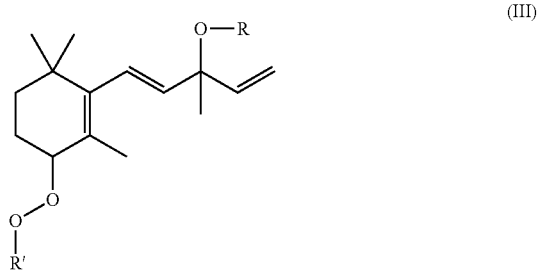

In formula III, R has the meanings given for formula I, in particular the meanings stated there as being preferred, and specifically represent hydrogen. R' is hydrogen, alkyl or aryl. R' is in particular other than hydrogen. R' is in particular tertiary $C_4$-$C_6$-alkyl such as tert-butyl or 1,1-dimethylpropyl (=tert-amyl) or tertiary phenyl-$C_3$-$C_8$-alkyl, where the phenyl radical is unsubstituted or may carry 1, 2 or 3 $C_1$-$C_4$-alkyl groups, and is for example 2-phenyl-2-propyl (cumyl).

The compound III can be separated from the primary reaction mixture, for example via the chromatographic route, for example by means of column chromatography on silica gel, using ethyl acetate/$C_6$-$C_8$-alkane mixtures or tetrahydrofuran/$C_6$-$C_8$-alkane mixtures. Usually, however, the compound will be reacted further to give the compound I, for example by heating and/or further addition of transition metal and/or by addition of a base, in particular a nitrogen base, especially with addition of a secondary or tertiary amine or an oxo base, or the compound III is converted spontaneously into the compound of the formula I, for example upon prolonged reaction times and/or higher reaction temperatures.

The compounds of the formula III are novel and likewise subject matter of the present invention.

The reaction mixture generated upon the oxidation of II is worked up in the customary manner. To destroy an excess of oxidant, the latter will optionally be decomposed before the compound I is isolated, for example by adding a reducing agent such as, for example, sodium sulfite, sodium hydrogen sulfite, iron(II) sulfate or sodium thiosulfate. The further work-up can be performed by extractive or in any other manner. Thereafter, the resulting compound of the formula I is optionally purified, for example by distillation or chromatography or by combinations of these methods.

The invention furthermore relates to the preparation of compounds of the formula IV, which comprises, in a first step, the preparation of a compound of the general formula I by the process according to the invention, and, in a second step, the conversion of the compound of the formula I into the compound of the formula IV in a manner known per se. For example, the conversion of the compound of the formula I in which X is OH and R is hydrogen or an OH protecting group, preferably an acid-cleavable OH protecting group, for example a group of the formula $SiR^aR^bR^c$ or an acetal protecting group, may be effected by the method described in EP 101597 and EP 490326.

Analogously to the method described in EP 101597, it is possible, for example, to convert the compound of the formula I into a silyl enol ether of the formula V.

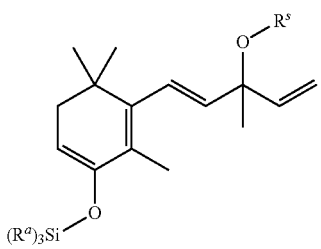

(V)

In formula V, the radicals $R^a$ in group $Si(R^a)_3$ may be identical or different and they are, independently of one another, $C_1$-$C_4$-alkyl and especially methyl or ethyl. $R^s$ is an OH protecting group, preferably an OH protecting group which is cleavable by an acid or by treatment with an acid, for example a group of the formula $SiR^aR^bR^c$ or an acetal protecting group, and specifically a group $Si(R^a)_3$.

The conversion of the compound I to the compound of the formula V is successfully carried out for example by reacting a compound of the formula I with a trialkylsilyl halide or pseudohalide of the formula $HalSi(R^a)_3$, where Hal is halogen and in particular chlorine or a pseudohalide, in particular mesilate or triflate. Particularly preferably, the conversion to the compound of the formula V is successfully carried out when a compound of the formula $HalSi(R^a)_3$ is used, in which Hal is mesilate or triflate and in which $R^a$ is preferably methyl or ethyl. The compound $HalSi(R^a)_3$ is typically used in the stoichiometrically required amount or in excess, in the case of the compound I where R=H, preferably in the range 2 to 10 equivalents, in particular in an amount of 5 to 9 equivalents, based on the quantitative amount of compound of the formula I where R=H. If, in the employed compound of the formula I, the variable R is hydrogen, this gives rise to a silyl enol ether of the formula V in which $R^s$ is a group $Si(R^a)_3$.

The reaction of the compound I to give the compound of the formula V usually takes place in the presence of a tertiary amine, for example a tri-$C_1$-$C_4$-alkylamine or di-$C_1$-$C_4$-alkyl-$C_5$-$C_8$-cycloalkylamine such as triethylamine, diisopropylethylamine, tri-n-propylamine, diethylcyclohexylamine, an amidine base such as 1,5-diazabicyclo-[4.3.0]non-5-ene (DBN) or 1,8-diazabicyclo[5.4.0]undec-7-ene (DBU) or a polycyclic amine such as 1,4-diazabicyclo[2.2.2]octane (DABCO). Particular preference is given to triethylamine. The amount of tertiary amine is typically in the range from 2 to 15 equivalents, in particular in the range from 6 to 11 equivalents, based on the quantitative amount of compound of the formula I where R=H.

The reaction of the compound I to give the compound of the formula V generally takes place in an organic solvent or solvent mixture. Suitable solvents are in particular aprotic solvents, such as, for example, N,N-dimethylformamide, N,N-dimethylacetamide, tetrahydrofuran, methyltetrahydrofuran, dichloromethane, dichloroethane, acetonitrile, propylene carbonate and toluene, and mixtures thereof. Usually, the solvent is used in an amount in the range from 0.5 to 10 g, in particular 1 to 3 g per g of compound of the formula I.

Optionally, the reaction of the compound I to give the compound of the formula V can be carried out in the presence of a phase transfer catalyst, for example a tetra-$C_1$-$C_{12}$-alkylammonium salt, in particular in the presence of a tetra-$C_1$-$C_{12}$-alkylammonium hydroxide, chloride, bromide, iodide, mesilate or triflate, such as tetrabutylammonium hydroxide, tetrabutylammonium chloride, tetrabutylammonium bromide, tetrabutyl-ammonium iodide, tetrabutylammonium mesilate, tetrabutylammonium triflate and/or in the presence of a di-$C_1$-$C_4$-alkylaminopyridine such as 4-dimethylaminopyridine.

As regards further details, reference is here by made to EP 101597, in particular to pages 5 and 6 and examples 6 and 8.

Thereafter, the silyl enol ether of the formula V is reacted with a peroxocarboxylic acid, for example peracetic acid, perbenzoic acid or monoperphthalic acid, which gives the compound of the formula VI:

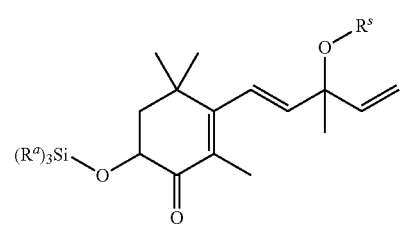

(VI)

in which the radicals $R^a$ in groups $Si(R^a)_3$ can be identical or different and independently of one another are $C_1$-$C_4$-alkyl and in which $R^s$ has the meanings mentioned hereinabove for the silyl enol ether of the formula V, and in particular a group of the formula $Si(R^a)_3$. Here, the compound of the formula (VI) is often produced in the mixture with the compound of the formula VIIIa, and/or, if $R^s$ in formula V is a group of the formula $Si(R^a)_3$, in the mixture with the free alcohol of the formula VII.

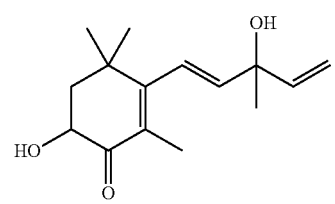

(VII)

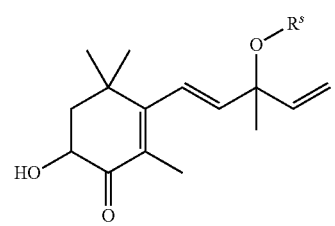

(VIIa)

In formula VIIa, $R^s$ is an OH protecting group, in particular an OH protecting group which can be cleaved off by acid, specifically an acetal protecting group or very specifically a group $Si(R^a)_3$, where $R^s$ are identical or different and are $C_1$-$C_4$-alkyl.

Cleaving off the protecting group $R^s$ from the compound VI or VIIa and optionally the group $Si(R^a)_3$ from the compound VI, for example by hydrolysis of the compound of the formula VI, for example using trialkylammonium hydrofluoride, if $R^s$ is $Si(R^a)_3$, subsequently yields the compound of the formula VII.

As regards further details, reference is made herewith to EP 101597, in particular to pages 5 and 6 and examples 7 and 9.

The successive reaction of the compound of the formula VII with a halogenating agent, preferably a hydrogen halide HZ, in particular hydrogen bromide, followed by reaction with triphenylphosphane, gives the compound of the formula IV in which X is OH in good yields. Preferably, excess hydrogen halide HZ will be removed using triphenylphosphane before carrying out the reaction. In particular, it has proved advantageous to remove, before carrying out the reaction with triphenylphosphane, any traces of hydrogen halide by adding alkylene oxide, such as butylene oxide, (cf. Helv. Chim. Acta 64, 2444, 1981).

The phosphonium salt can be purified by crystallization and scrubbing, or recrystallization. In particular, dichloromethane, dichloroethane, chlorobenzene, toluene, heptane, cyclohexane, methylcyclohexane, THF, isopropanol, isobutanol, acetic acid $C_1$-$C_4$-alkyl ester, acetonitrile or acetone, individually or mixtures thereof, are employed for crystallization or recrystallization.

Alternatively, the compound IV may be prepared by first converting a compound of the formula I in which R is an OH protecting group, in particular an acid-cleavable OH protecting group $R^s$ and in particular a group $Si(R^a)_3$, where $R^a$ are identical or different and $C_1$-$C_4$-alkyl, into its enolate. The conversion into the enolate is successfully carried out by reacting I with a strong base, for example an alkali metal amide such as lithium diisopropyl amide, lithium (hexamethyldisilazane), sodium (hexamethyldisilazane) or potassium (hexamethyldisilazane), analogously to the method described in EP 490326. The enolate thus obtained is subsequently reacted with an N-arylsulfonyloxaziridine, for example N-phenylsulfonyl-3-phenyloxaziridine, giving rise to the compound of the formula VIIIa defined above.

As regards further details, reference is made herewith to EP 490326, in particular to the examples therein.

Cleaving off the protecting group $R^s$ from the compound of the formula VIIIa, for example by acid hydrolysis, and reacting the resulting product with a halogenating agent, for example a hydrogen halide and subsequently with triphenylphosphane analogously to the method described in EP 101597 gives the compound of the formula IV in which X is OH in good yields.

Analogously, the compound of the formula I in which R is H can be converted into the compound of the formula IV in which X is hydrogen by reacting I with halogenating agent, for example a hydrogen halide or phosphorus trihalide, for example phosphorus tribromide, and subsequently with triphenylphosphane analogously to the method described in EP 101597.

During the experiments into the conversion of the compound I into the compound IV in which X is OH, it has, surprisingly, been found that, contrary to the teaching in the literature, deprotecting the compound of the formula VI in which $R^s$ is an acid-cleavable OH protecting group, preferably an acetal protecting group and in particular a group $Si(R^a)_3$, which compound of the formula VI is formed during the oxidation of the silyl enol ether of the formula V is not required in order to obtain the compound IV where X=Br. Rather, it suffices successively to react the silyl enol ether of the formula VI with hydrobromic acid, that is an aqueous solution of hydrogen bromide, and subsequently with triphenylphosphane, which gives the compound of the formula IVa in very good yields:

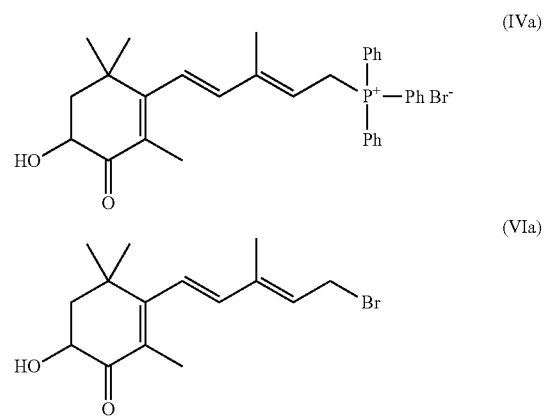

It is not necessary to isolate the compound of the formula VIa, which is formed during the reaction of compound VI with hydrobromic acid. Rather, the reaction mixture obtained during the reaction of compound VI with hydrobromic acid can be reacted directly with triphenylphosphane. Preferably, excess hydrogen bromide will be removed before reacting with triphenylphosphane. In particular, it has proved advantageous to remove any traces of hydrogen bromide by adding alkylene oxide, such as butylene oxide, before reacting with triphenylphosphane (cf. Helv. Chim. Acta 64, 2444, 1981).

This procedure shortens the synthesis of the compound IVa by a further reaction step. Accordingly, the present invention also relates to a process for the preparation of a phosphonium salt of the formula IVa which comprises the following steps:

a") providing a silyl enol ether of the formula V as defined above, in which $R^s$ is an OH protecting group which can be cleaved off by acid treatment, preferably an acetal protecting group or in particular a group $Si(R^a)_3$ in which $R^a$ are identical or different and are $C_1$-$C_4$-alkyl;

b") successively reacting the compound of the formula V with a peroxocarboxylic acid and reacting the oxidation product of the formula VI with hydrobromic acid, which gives a compound of the formula VIa;

c') reacting the compound of the formula VIa with triphenylphosphane, which gives a compound of the formula IVa.

The reaction of the oxidation product of the formula VI with hydrobromic acid will, as a rule, be carried out using a 10 to 60% by weight strength, in particular 20 to 50% by weight strength, aqueous solution of hydrogen bromide. As a rule, hydrogen bromide is employed in an excess based on the stochiometry, for example in an amount of from 1.5 to 2.5 mols per mole of the compound VI. The reaction of VI with hydrobromic acid is typically carried out at temperatures in the range from −20° C. to +25° C., in particular in the range of from −10° C. to +10° C. The compound of the formula VIa, which is generated during the reaction, may be isolated before it is reacted further, but this will not be necessary in most cases.

The examples which follow are intended to illustrate the invention in greater detail. The following abbreviations are used:

HPLC: high-performance liquid chromatography
GC: gas chromatography
THF: tetrahydrofuran
DMF: N,N-dimethylformamide
DCM: dichloromethane
NMP: N-methylpyrrolidone
tert-BuOOH: tert-butyl hydroperoxide Salen: ligand B1
OAc: acetate
OTf: trifluoromethanesulfonate
acac: acetylacetonate (pentan-2,4-dionate)
OVI: oxovinylionol (compound of the formula I where R=H)
tBOOVI: tert-butylperoxyvinylionol (compound of the formula III where R=H)
Eq: equivalent
TEA: triethylamine
TMEDA: N,N,N',N'-tetramethyl-1,2-ethanediamine
TBACI: tetrabutylammonium chloride
TBAOH: tetrabutylammonium hydroxide
TBAB: tetrabutylammonium bromide
TBAI: tetrabutylammonium iodide
Triton-X: octylphenol ethoxylate
TMSCl: trimethylsilyl chloride
TMSOMs: trimethylsilyl methylsulfonate
DMAP: 4-(dimethylamino)pyridine
DBU: 1,8-diazabicyclo[5.4.0]undec-7-ene
I. Analyses
All reaction mixtures were analyzed for their composition by HPLC, using the method described hereinbelow unless otherwise specified.
Equipment: Agilent series 1200
Column: Ascentis Express $R^P$-Amide 2.7 μm 100*3 mm by Supelco®
Detector: UV detector X=242 nm, BW=4 nm
Eluent: —A: water containing 0.02% by volume of ethylenediamine
—B: acetonitrile

| Time in min | % B | Flow rate |
| --- | --- | --- |
| 0.0 | 30 | 0.6 |
| 6.0 | 70 | 0.6 |
| 7.0 | 100 | 0.6 |
| 9.0 | 100 | 0.6 |
| 9.1 | 30 | 0.6 |

Measuring conditions:
Injection: 5 μl
Temperature: 50° C.
Chromatography time: 12 min
Pressure: approx. 160 bar Calibration was achieved with an external standard, following the protocol hereinbelow. The pure substances are weighed in at the following concentrations:
1. approx. 0.05 g/50 ml
2. approx. 0.10 g/50 ml
3. approx. 0.15 g/50 ml
4. approx. 0.20 g/50 ml
5. approx. 0.25 g/50 ml The samples were dissolved in acetonitrile. The samples were weighed accurately to 0.1 mg. A calibration curve is generated using a suitable PC program. This is a linear function for the substances used. The standard deviation, the correlation coefficient and the straight-line equation are calculated and are a measure for the goodness of the calibration. In this way, the concentration of the components can be determined in relation to the respective external standard.

The HPLC was evaluated by subtracting the eluent spectrum from the sample spectrum. The range up to 11 minutes was evaluated, while the remainder of the running time was used for the equilibration. The percentage by weight, of the starting material, is calculated from the peak area using the following equation:

$$\text{Percent by weight }(ESTD\ \%) = \frac{\text{Peak area} \times 100 \times \text{response factor}_{(substance)}}{(\text{sample}) \text{ weight}}$$

The response factor is the quotient from the sample weight of the reference substance and the peak area of the reference substance.

EXAMPLE 1

15 g of vinylionol (96%, 0.068 mol) in 146 g of pyridine were treated with 0.22 g (0.002 mol) of CuCl and the mixture was heated to 35° C., with stirring. In the course of 90 minutes, this mixture was triggered with 26.3 g (0.204 mol) of a 70% by weight aqueous solution of tert-butyl hydroperoxide, and the resulting mixture was stirred for 22 h at 35-40° C. Quantitative HPLC of the reaction product revealed 46.4% by weight of the product, with the reaction of starting material being complete.

The aqueous phase was separated off and reextracted twice using in each case 60 g of toluene. The combined organic phases were washed once with 50 g of semisaturated aqueous sodium sulfite solution and twice using in each case 50 ml of water, dried over $Na_2SO_4$ and evaporated to dryness under reduced pressure. 16.6 g of product phase comprising 38.4% of product (compound I, R=H).

The resulting compound of the formula I (R=H) can be purified for further use by standard purification operation, such as, for example, column chromatography or fractional distillation.

EXAMPLE 2

15 g of vinylionol in 145 g of pyridine were treated with 2.24 g of Co(II) acetylacetonate (0.009 mol). In the course of 60 minutes, this mixture was treated, at 40° C., with 26.3 g (0.204 mol) of a 70% by weight aqueous solution of tert-butyl hydroperoxide. The reaction mixture was then heated at 60° C. for 16 h. To complete the reaction, heating was continued for 24 h at 70° C. According to HPLC, the mixture comprised 35.3% by weight of the peroxide compound III (R=H, R'=tert-butyl) and 22% by weight of product (compound I, R=H) and 8% by weight of starting material (compound II, R=H).

EXAMPLE 3

Analogously to example 1, 10 g of vinylionol in 214 g of acetonitrile were reacted in the presence of 0.095 g of CuI and 33.4 g of 70% by weight strength aqueous solution of tert-butyl hydroperoxide. This gave a product mixture which, according to HPLC, comprised 25% by weight of product (compound I, R=H).

EXAMPLE 4

20 g of vinylionol and 1.56 g of $CoCl_2$ were heated to 60° C. in 65 g of pyridine. In the course of 180 minutes, 36.6 g (3 eq.) of a 70% by weight strength aqueous solution of tert-butyl hydroperoxide were added. The reaction mixture was then stirred at 60° C. for a further 16 h. Thereafter, a further 36.6 g (3 eq.) of a 70% by weight strength aqueous solution of tert-butyl hydroperoxide were then added dropwise in the course of 2 h. According to HPLC, the mixture comprised 50% of the peroxide III (R=H, R'=tert-butyl), and 3% by weight of starting material (compound II, R=H) and 42% by weight of product (compound I, R=H). Stirring was continued for 20 h at 60° C., a further 12.2 g (1 eq.) of a 70% by weight strength aqueous solution of tert-butyl hydroperoxide was added in the course of 1 h, and stirring was continued for 5 h at 60° C. According to HPLC, the mixture was composed to 50% by weight of the desired product and to 4.8% by weight of peroxide.

EXAMPLE 5

Analogously to example 1, 15 g of vinylionol in 146 g of pyridine were reacted in the presence of 8.2 mmol (0.128 eq.) of $CuCl_2$ and 24.7 g (3 eq.) of a 70% by weight aqueous solution of tert-butyl hydroperoxide. After a reaction time of 4 h, a product mixture which, according to HPLC, comprised 33.2% by weight of product (compound I, R=H) was obtained.

EXAMPLE 6

28 g of water and 0.114 g of $RuCl_3$ were introduced into a reaction vessel, and a solution of 19.5 g of vinylionol in 200 ml of cyclohexane was added, with stirring. 113.9 g of a 70% by weight strength aqueous solution of tert-butyl hydroperoxide were added to this mixture in the course of 6 h, at 15-20° C. The mixture was stirred for 18 h. Thereafter, the organic phase was separated off and divided into two portions.

The first half was washed with 100 ml of saturated aqueous sodium sulfite solution, dried over sodium sulfate and subsequently evaporated to dryness. According to HPLC, the residue comprised 21.7% by weight of product (compound I, R=H) and 2.3% by weight of the peroxide 111 (R=H, R'=tert-butyl).

As an alternative, the second half was treated with 200 ml of water and 250 ml of 2-butanone. 19.5 g of $Na_2SO_3$ were added, and the mixture was stirred for 3 h at 70° C. After cooling, the phases were separated, and the organic phase was dried and evaporated to dryness at 50° C. under reduced pressure. According to HPLC, the residue comprised 21.3% by weight of product (compound I, R=H) and 2.6% by weight of the peroxide 111 (R=H, R'=tert-butyl).

EXAMPLE 7

The peroxide 111 (R=H, R'=tert-butyl) isolated by a repeated chromatography of the reaction product of example 1 in on each case 70 g of silica gel using a mixture of heptane/THF as a viscous oil.

$^1$H NMR ($CDCl_3$, 400 MHz: 6.1-5.9 (m, 2H), 5.6 (d, 1H), 5.3 (d, 1H), 5.1 (d, 1H), 4.2 (br. S. 1H), 2.1-2.0 m, 1H), 1.8 (s, 3H), 1.7-1.6 (m, 2H), 1.6 (m, 1H), 1.4 (s, 3H), 1.4-1.3 (m, 1H), 1.4 (s, 9H), 1.0 (2×s, 6H).

EXAMPLE 8

30 g of vinylionol (0.136 mol) in 97 g of pyridine were treated with 0.911 g of 00012 and heated to 60° C. In the course of 180 min, 53.8 g of a 70% by weight strength aqueous solution of tert-butyl hydroperoxide were added, and the mixture was stirred for 17 h at 60° C. The reaction mixture obtained comprised 27.3% of the desired product (compound I, R=H), 4.1% of the starting material and 25.7% of the peroxide 111 (R=H, R'=tert-butyl).

Thereafter, the reaction mixture was added dropwise in the course of 6 h into a mixture, heated to 70° C., of 0.397 g of CuI in 74 g of pyridine. Thereafter, HPLC reveals 43.5% by weight of product 1, 3.5% of starting material and only 1.6% of peroxide III. To the mixture there was added 1 eq. of tert-butyl hydroperoxide, and stirring of the mixture was continued for 16 h at 60° C. Thereafter, the reaction mixture was treated with 125 ml of toluene, 450 g of water were added, and the phases were separated. The organic phase was washed once with semiconcentrated aqueous $NaHSO_3$ solution and twice with water and then concentrated. This gave 17 g of crude product which comprised 38.7% by weight of the desired product (compound I, R=H). This corresponds to a yield of 43%.

EXAMPLE 10

0.11 mol of vinylionol (compound II, R=H) were treated with 191 mg of 1,10-phenanthroline and 563 mg of Co(II) (2-ethylhexanoate)$_2$ (65% strength by weight in white oil). The reaction mixture was heated to 60° C. 45 g of tert-butyl hydroperoxide (70% in water) were then added such that the temperature was kept at about 60° C. The mixture was then stirred until further conversion could no longer be observed, 19.9 g of piperidine were added and the mixture was heated to 70° C. until the concentration of the intermediate product of the formula III (R=H) altered no more.

For work-up, the reaction mixture was treated with 26 g of toluene and 50 g of semi-saturated sodium chloride solution and the phases were separated. The aqueous phase was back-extracted with 26 g of toluene and the combined organic phases were washed with 50 g of water. Removing the volatile constituents of the organic phase gave 30.3 g of crude product with a fraction of 32.7% of compound of the formula I (R=H).

EXAMPLE 11

Analogously to example 11, 0.10 mol of vinylionol in 20.7 g of DMF with 556 mg of Co(II) (2-ethylhexanoate)$_2$ and 0.184 g of 1,10-phenanthroline were slowly treated with 44.54 g of 70% tert-butyl hydroperoxide (in water) at 68 to 72° C. Here, the Co(II) (2-ethylhexanoate)$_2$ and the phenanthroline were each added in 2 aliquots before the peroxide was added and after half of the peroxide had been added. 16.07 g of triethylamine were then added and the mixture was stirred at 70° C. until an increase in product I could no longer be observed. Aqueous work-up as in example 10 produced 29.6 g of crude product with a content of compound I (R=H) of 33.1% by weight.

EXAMPLE 12

Analogously to example 10, 0.1 mol of vinylionol in 12.3 g of acetonitrile and in the presence of 0.8 g of Co(acac)$_3$ and 0.4 g of 1,10-phenanthroline were reacted with 38.6 g of tert-butyl hydroperoxide and then stirred with 20.2 g of triethylamine until no further product increase was observed. Work-up as in example 10 gave 23.9 g of crude product which corresponded to a yield, based on % by weight, of 41% of product of the formula I (R=H).

EXAMPLE 13

0.1 mol of vinylionol was dissolved in 8.4 g of pyridine. The solution was admixed with 164 mg of 1,3-oxazole and 150 mg of Cu(I) oxide and heated to 40° C. and reacted analogously to example 10 with 45.3 g of tert-butyl hydroperoxide. The mixture was then heated to 70° C. until an increase in the product of the formula I (R=H) was no longer observed. Work-up as described in example 10 gave the compound of the formula I (R=H) in 32% strength yield as crude mixture.

EXAMPLE 14

0.3 mol of vinylionol was treated in 70 g of pyridine with 0.79 g of Co(II) (2-ethyl-hexanoate)$_2$ and, at 90° C., 126 g of 70% strength aqueous tert-butyl hydroperoxide solution were added dropwise, with a further 0.79 g of Co(II) (2-ethylhexanoate)$_2$ being added after half of the amount of tert-butyl hydroperoxide solution had been added. The reaction mixture was then heated to 98° C. while distilling off low-boiling components until intermediate product III (R=H) could no longer be detected. Following work-up analogously to example 10, the compound of the formula I (R=H) is isolated as crude product in a yield of 33%.

EXAMPLES 15a to 15m 1 to 2 mol % of the metal salt/complex given in the table below were introduced into 1.5 g (6.8 mmol) of vinylionol, and 2.92 g (22.7 mmol) of 70% strength aqueous tert-BuOOH solution in 2.7 g (34.1 mmol) of pyridine were metered in in 3 portions at a rate in each case of 1 ml/min. The mixtures were then stirred for 10 h at 40° C. and analyzed for the formation of the compound I (R=H) and compound III (R=H) in the manner described above. The results are summarized in table 1 below.

TABLE 1

| | Transition metal compound | | OVI | tBOOVI |
|---|---|---|---|---|
| Example | Metal | Compound | Yield [%][1] | Yield [%][1] |
| 15a | Cu(I) | Cu$_2$O | 30.9 | 37.6 |
| 15b | Cu(I) | [Cu(CH$_3$CN)$_4$]PF$_6$ | 29.0 | 30.5 |
| 15c | Cu(II) | CuBr$_2$ | 38.8 | 14.8 |
| 15d | Cu(II) | Cu(OAc)$_2$ | 41.7 | 23.2 |
| 15e | Cu(II) | Cu(OTf)$_3$ | 34.2 | 23.7 |
| 15f | Cu(II) | Cu(acac)$_2$ × H$_2$O | 46.6 | 5.9 |
| 15g | Co(II) | CoBr$_2$ | 16.9 | 42.8 |
| 15h | Co(II) | CoI$_2$ | 4.4 | 24.7 |
| 15i | Co(II) | Co(BF$_4$)$_2$ | 8.8 | 27.0 |
| 15k | Co(II) | Co(OAc)$_2$ × 4H$_2$O | 16.7 | 25.0 |
| 15l | Co(II) | Co(format)$_2$ × 2H$_2$O | 7.6 | 28.8 |
| 15m | Co(II) | Co-phthalocyanine | 21.4 | 14.1 |

[1]Yield based on vinylionol used

EXAMPLES 16A TO 16V

Analogously to example 11, vinylionol in DMF or NMP was reacted firstly with tBuOOH. The resulting reaction was then further reacted in accordance with the details in table 2 with a base to give the end product of the formula I (R=H). The yields are given in table 2:

TABLE 2

| Ex. | Temp. | Base/Amount[1] | Time [h] | Yield of OVI[2] |
|---|---|---|---|---|
| 16a | 70° C. | Piperidine/1.0 eq. | 19 | 41.5% |
| 16b | 70° C. | TEA/1.0 eq. | 19 | 43.3% |
| 16c | 70° C. | Morpholine/1.0 eq. | 19 | 34.1% |
| 16d | 70° C. | Na methylate/1.0 eq. | 19 | 41.2% |
| 16e | 70° C. | Aqueous NaOH 50%/1.0 eq. | 19 | 40.8% |
| 16f | 70° C. | Aqueous KOH 50%/1.0 eq. | 19 | 40.3% |
| 16g | 70° C. | Potassium tert-butylate/1.0 eq. | 19 | 40.1% |
| 16h | 70° C. | NaHCO$_3$/1.0 eq. | 19 | 28.8% |
| 16i | 70° C. | Na$_2$CO$_3$/1.0 eq. | 19 | 26.7% |
| 16k | 70° C. | TEA/1.1 eq. | 16 | 43.0% |
| 16l | 70° C. | TEA/2 eq. | 23 | 43.6% |
| 16m | 70° C. | Piperidine/1.0 eq. | 12 | 43.2% |
| 16n | 70° C. | Tripropylamine/2 eq. | 12 | 40.3% |
| 16o | 70° C. | TMEDA/1 eq. | 12 | 34.4% |
| 16p | 70° C. | N,N-Dimethylethanolamine/2 eq. | 12 | 35.6% |
| 16q | 70° C. | 2-Methylaminoethanol/2 eq. | 12 | 35.6% |
| 16r | 70° C. | NaOH 25%/1.0 eq. | 5 | 22.7% |
| 16s | 70° C. | NaOH 50%/1.0 eq. 20 mol % Triton-X | 12 | 35.3% |
| 16t | 70° C. | NaOH 50% strength 1 eq. 20 mol % TBACl | 12 | 32.5% |
| 16u | 70° C. | NaOH 50% strength/1 eq. 20 mol % TBAOH | 12 | 32.2% |
| 16v | 70° C. | NaOH 50% strength/1 eq. 10 mol % TBACl | 12 | 33.9% |

[1]Quantitative data based on vinylionol
[2]Yield of oxovinylionol, based on vinylionol Analysis for Compound V All crude discharges for producing V were analyzed for their composition by gas chromatography (GC) in accordance with the method described below unless specified otherwise.

Instrument Settings and Chromatographic Conditions:

Instrument: Agilent 6890 N

Carrier gas: Nitrogen

Separating column: Chrompack/50 m CP—Sil 5/ID=0.25 mm, FD=0.12 μm

Injection system: HP split/splitless injector/mode split 1: 109

Injection: HP-GC injector 7683 Series/Amount=1 μl

Detection: HP-FID

Temperatures+Pressures:

Detector: 300° C.

Injector: 250° C.

Starting temp.: 50° C.

Residence time 1: 0 min

Rate 1: 10° C./min

End temp. 1: 300° C.

residence time 2: 15 min

Run time total: 40 min

Pressure (prgm): 10.77 PSI constant

Septum purge: 0.6 ml/min

Sample Preparation:

The samples are dissolved to ca. 20% strength. Solvent suppression from 0-8 min.

Evaluation/Software:

$$\text{area percent } (N\ \%) = \frac{\text{Peak area } (iA) \times 100}{\text{Total area } (A)}$$

Retention time: Oxovinylionol (Formula I; R=hydrogen)=22.461 min Silyl enol ether (Formula V; R$^a$=CH$_3$, R$^s$=Si(CH$_3$)$_3$)=24.030 min

EXAMPLE 17

Preparation Example for Compound VI, $R^a=CH_3$, $R^s=Si(Ch_3)_3$

After purification by column chromatography on silica gel (ethyl acetate/heptane), the compound of example 1 was converted into the silyl enol ether of the formula V ($R^a$ $CH_3$, $R^a=Si(CH_3)_3$) analogously to example 6 of EP 101597. This silyl enol ether was converted into the compound of the formula VI ($R^a=CH_3$, $R^s=Si(CH_3)_3$) analogously to example 8, step a) of EP 101597.

EXAMPLES 18A TO 18L

Examples for the Preparation of the Silyl Enol Ether of the Formula V (1-5 G of the Compound I)

The compound of the formula I (R=H) was dissolved in the stated solvent with the amine base (and possibly a further addition e.g. a phase transfer catalyst) in the ratios listed in table 3 (based on the pure substance of the compound I) at room temperature. The corresponding silylating reagent was then added dropwise with the equivalents given in table 3 (based on the pure substance of the compound I) over the course of 1-2 minutes, and the mixture was stirred for a further 10 minutes at room temperature. The reaction mixture was then stirred at reflux for 16 h until no further conversion could be detected. For the analytical investigation (GC area %), a sample (2.5 ml) of the mixture was taken, treated with toluene (2.5 ml) and ice-water (2.5 ml) and washed at low temperature. Following phase separation, the organic phase was dried over $Na_2SO_4$ and the filtrate was analyzed by gas chromatography.

Preparation of the Silyl Enol Ether (V) and its Oxidation

HPLC analysis for the oxidation products VI and VIIa
Instrument: Agilent Series 1100
Column: Zorbax Eclipse XDB C18 1.8 μm 50*4.6 mm from Agilent®
Eluent: —A: Water with 0.05% by volume triethylamine
—B: Tetrahydrofuran

| Time in min | % B | Flow |
|---|---|---|
| 0.0 | 15 | 1.2 |
| 6.0 | 60 | 1.2 |
| 8.0 | 100 | 1.2 |
| 10.0 | 100 | 1.2 |
| 10.1 | 15 | 1.2 |

Detector: UV detector λ=250 nm, BW=5 nm
Flow rate: 1.2 ml/min
Injection: 5 μl
Temperature: 50° C.
Run time: 12 min
Pressure: ca. 200 bar
Sample Preparation:

A corresponding amount of sample was dissolved in tetrahydrofuran. In the case of pure substances, an initial weight of 15 mg per 10 ml of solvent was chosen in order to obtain good dissolution of the impurities. Samples which did not completely dissolve in tetrahydrofuran and/or water were filtered.

Evaluation/Software:

The eluent spectrum was subtracted from the sample spectrum. The range up to 10 minutes was evaluated; the remaining run time served only to further equilibrate the system.

TABLE 3

| Ex. | Reagent | Eq.[1] | Base | Eq[1] | Solvent [g/g][2] | V[3] | Remarks[4] |
|---|---|---|---|---|---|---|---|
| 18a | TMSCl | 6.8 | TEA | 8.7 | DMF 1.4 | 90.2 | — |
| 18b | TMSCl | 6.2 | TEA | 7.9 | DMF 1.3 | 92.0 | Addition of 0.05 eq. of each of TBAB and DMAP |
| 18c | TMSCl | 6.6 | TEA | 8.4 | Acetonitrile 1.4 | 92.2 | — |
| 18d | TMSCl | 5.0 | TEA | 6.7 | Acetonitrile 1.3 | 91.7 | Addition of 0.05 eq. of TBAB |
| 18e | TMSCl | 5.1 | TEA | 6.3 | Acetonitrile 1.3 | 92.6 | Addition of 0.05 eq. of TBAB |
| 18f | TMSCl | 5.1 | TEA | 6.3 | Acetonitrile 1.3 | 92.9 | Addition of 0.05 eq. of TBAI |
| 18g | TMSOMs | 8.2 | TEA | 10.5 | Acetonitrile 1.7 | 78.0 | — |
| 18h | TMSOMs | 6.7 | TEA | 9.8 | Acetonitrile 1.7 | 79.2 | — |
| 18i | TMSOMs | 6.4 | TEA | 8.1 | DCM 1.3 | 87.2 | — |
| 18k | TMSOMs | 6.5 | TEA | 8.2 | DCM 1.3 | 87.8 | Addition of 5 mol % of DMAP |
| 18l | TMSOMs | 6.5 | TEA | 8.2 | DCM 1.3 | 87.3 | Addition of 5 mol % of DBU |

[1]Equivalents based on the quantitative amount of the compound of the formula I (R = H)I
[2]Amount of solvent in g per g of oxovinylionol
[3]in GC area %
[4]Quantitative data, based on oxovinylionol When using TMSOMs in the presence of corresponding amine bases and depending on the solvent used, after the end of the reaction and the cooling phase but prior to the aqueous work-up, a liquid lower phase (ammonium mesilate) was separated off.

$$\text{Area percent } (A\ \%) = \frac{\text{Peak area}}{\text{Total area}} \times 100\%$$

Retention time: Compound of the formula VI ($R^a$=CH$_3$, $R^s$=Si(CH$_3$)$_3$)=7.474 min
Compound of the formula VIIa ($R^s$ =Si(CH$_3$)$_3$)=5.898 min

EXAMPLE 19

23.0 g (136.6 mmol) of hydrobromic acid (48% by weight) were introduced into the reaction vessel at −5° C. A solution of 27.3 g of the compound of the formula VI of example 17 in 240 ml of dichloromethane was added at −5 to 0° C., and the mixture was subsequently stirred for 40 min at 0° C. Thereafter, the reaction mixture was treated with ice-water (36 ml). After the aqueous phase had been separated off, the organic phase was washed with 38 g of aqueous NaHCO$_3$ solution (1.25% strength). The organic phase was again washed with water (43 ml). Thereafter, the resulting solution was treated with 0.33 ml of butylene oxide (1,2-epoxybutane) at room temperature. Thereafter, a solution of triphenylphosphane (17.9 g, 68.3 mmol) in toluene (26 ml) was added dropwise, and the mixture was again treated with butylene oxide (0.33 ml). After a reaction time of 1 h at room temperature, the reaction solution was heated to reflux and a solvent exchange from dichloromethane to toluene was carried out at atmospheric pressure. The solution was cooled (0-5° C.), and the crystallisate generated was filtered off with suction, washed with toluene and dried overnight in a stream of N2. This gave 27.4 g of the phosphonium bromide of the formula IVa as a pale ochre solid (melting point 167-169° C.).

EXAMPLE 20

With stirring, compound of the formula I (167.5 mmol) was introduced into acetonitrile (80.0 ml), triethylamine (177.08 g) and tetrabutylammonium bromide (4.03 g) at room temperature. 149.38 g of TMSCl were then added dropwise to the mixture over the course of 45 min at 20-25° C. When the addition was complete, the mixture was stirred for a further 5 min at 20-25° C. and then the resulting suspension was heated at reflux for 24 h. The mixture was cooled to 0° C. and treated with 750 ml of toluene. Water (250 ml) was then added dropwise over the course of 1 h at 0-5° C. When the addition of water was complete, the mixture was stirred for a further 15 min before the phases were separated. The upper phase was then washed 3× with in each case 250 ml of water at 0-5° C. The toluenic phase was treated, with stirring at 0° C., in succession with 27.08 g of anhydrous magnesium sulfate and 26.25 g of sodium hydrogencarbonate. Then, at 0-5° C., a total of 97.5 g of peracetic acid (aqueous, 39% strength by weight) were added dropwise at 0-5° C. over the course of 2 h. Following complete conversion (according to thin layer chromatography; cyclohexane:ethyl acetate 20:1), the reaction mixture was treated with vigorous stirring at 0° C. with a total of 500 ml of water and stirred for 10 min. Following phase separation, the upper phase was washed successively twice with 20% strength by weight aqueous sodium disulfite solution (in each case 250 ml), once with 250 ml of water and once with 2.5% strength by weight aqueous sodium hydrogencarbonate solution. The organic phase was dried over sodium sulfate, filtered and concentrated in vacuo (50° C., up to 10 mbar). The crude product (87.94 g) was present as a mixture of the compounds of the formulae VI (68.0 area %) and VIIa (11.6 area %) as a pale brown low viscosity oil. The ratio of the area % of VI and VIIa is generally variable on account of the differing progress of the hydrolysis of the silyl protecting group, and can be present for example after a prolonged dwell time in the ratio 1 (compound of the formula VI): 4 (compound of the formula VIIIa). The crude product obtained was used directly in the following synthesis.

With vigorous stirring, 63.22 g of aqueous HBr (48% strength) was introduced at 0° C. and, over the course of 30 min, the crude product from the preceding stage, as a mixture of the compounds of the formulae VI and VIIa (87.94 g) in 700 ml of methylene chloride, was added dropwise thereto. Following complete conversion (according to thin layer chromatography; cyclohexane:ethyl acetate 20:1), the reaction mixture was treated with 120 ml of water at 0° C. Following phase separation, the organic phase was washed successively with 2.5% strength sodium hydrogencarbonate solution (120 ml) and water (120 ml) at 0-5° C.

The organic phase was introduced at 20-25° C. and treated, with stirring, with 1,2-epoxybutane (901 mg). A solution of triphenylphosphine (53.77 g) in 100 ml of toluene was then added dropwise. Following complete addition, the reaction mixture was stirred for 1 h in total. The mixture was again treated with 1,2-epoxybutane (901 mg). The reaction mixture was heated at reflux and a solvent exchange of dichloromethane for toluene (1500 ml) was carried out at atmospheric pressure. The solution was cooled to 0-5° C. and stirred for 1 h at this temperature. The crystallisate was filtered off with suction and washed with 3×150 ml of toluene. The residue was dried overnight in an N2 stream and produced 77 g of the phosphonium bromide IVa (84.29 HPLC % by wt.) as a pale ochre-colored solid.

HPLC Analysis for Phosphonium Bromide IVa

The phosphonium salts IVa were analyzed for their composition by HPLC in accordance with the method described below unless specified otherwise.
Instrument: Agilent Series 1100
Column: LiChrospher® 60 R$^p$-select B 5 μm 250×4 mm
Eluent: —Gradient mode KH2PO$_4$ solution and acetonitrile
 —A=Acetonitrile
 —B=10 mmol KH2PO$_4$ solution pH=2.5 (adjusted with 85% strength H$_3$PO$_4$)

| Time  | % B | Flow |
|-------|-----|------|
| 0.00  | 60  | 0.8  |
| 20.00 | 30  | 0.8  |
| 40.00 | 30  | 0.8  |

Detector: DAD: λ=220 nm, band width 4
Flow rate: 0.8 ml/min
Injection: 20 μl
Temperature: 30° C.±0.5° C.
Run time: 45 min
Pressure: ca. 90 bar
Calibration:

The calibration was carried out with the help of external standards. The pure substance phosphonium bromide IVa was weighed into a 50 ml flask in the following amounts:
1. 5 mg
2. 10 mg
3. 20 mg
4. 30 mg
5. 40 mg The samples were dissolved in 50% by volume of eluent B and 50% by volume of water (ultrasound for 2 minutes) and then topped up. The accuracy of the initial weights was 0.1 mg. A suitable PC program was used to generate a calibration curve. For the substance listed above, this is a linear function. Standard deviation, correlation coefficient and straight-line equation were calculated and are a measure of the quality of the calibration. For the component, its concentration could thus be determined, relative to the particular external standard.

Sample Preparation:

The substance was dissolved in corresponding concentration in 50% by volume eluent B and 50% by volume water in a 50 ml flask. The sample prepared in this way could be measured directly.

Evaluation/Software:

$$\text{Percent by weight }(ESTD\ \%) = \frac{\text{Peak area} \times 100 \times \text{Response factor}_{(phosphonium\ salt)}}{\text{Initial weight (sample)}}$$

$$\text{Response factor}_{(phosphonium\ salt)} = \frac{\text{Initial weight (phosphonium salt)}}{\text{Area (phosphonium salt)}}$$

Retention time: Compound of the formula IVa:
    Isomer 1: 13.960 min; Isomer 2: 14.807 min

We claim:

1. A process for the preparation of oxovinylionol and its O-protected derivatives of the formula I

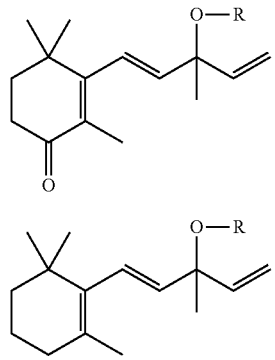

in which R is hydrogen or an OH protecting group, wherein β-vinyl ionol or an O-protected derivative thereof of the formula II in which R has the above mentioned meanings is reacted with an oxidant in the presence of at least one transition metal selected from the group consisting of Cu, Co, Fe, Mn, and mixtures thereof, where the oxidant comprises at least one oxygen-containing compound selected from among hydrogen peroxide and organic hydroperoxides.

2. The process according to claim 1, wherein the oxidant comprises an organic hydroperoxide which is selected from among alkyl hydroperoxides and arylalkyl hydroperoxides.

3. The process according to claim 2, wherein the organic hydroperoxide is selected from among tertiary $C_4$-$C_8$-alkyl hydroperoxides.

4. The process according to claim 1, wherein the oxidant is employed in an amount of from 1 to 10 mol per mole of the compound of the formula II.

5. The process according to claim 1, wherein the transition metal is employed in the form of a transition metal compound.

6. The process according to claim 1, wherein the transition metal is employed in the form of at least one compound which is selected from among CuCl, $CuCl_2$, CuI, $CoCl_2$, Cu(II) oxalate, Co(II) salts of organic monocarboxylic acids, such as Co(acetate)$_2$, Co(2-ethylhexanoate)$_2$ or Co(naphthenate)$_2$, Co(II)oxalate, Co(acac)$_2$, Co(acac)$_3$, Co(salen), Co(salen)Cl, Mn(salen) and Mn(salen)Cl, and Mn(acac)$_2$, where acac is acetylacetonate and salen is the N,N'-bis(salicylidene)ethylenediamino ligand.

7. The process according to claim 1, wherein the at least one transition metal is employed in a total amount of from $5 \times 10^{-6}$ to 0.5 mol per mole of the compound of the formula II.

8. The process according to claim 1, wherein the reaction with the oxidant is carried out in the presence of a complex ligand which has at least one nitrogen atom suitable for coordination with the transition metal.

9. The process according to claim 1, wherein the ligand has at least one group suitable for coordination with the transition metal which is selected from among oxazole, 2,2-bipyridine and 1,10-phenanthroline groups.

10. The process according to claim 1, wherein the ligand is used in an amount of from 0.5 to 2 mol per mole of transition metal.

11. The process according to claim 1, wherein the reaction is carried out in an organic solvent or in a mixture thereof with water.

12. The process according to claim 1, wherein the variable R in formulae I and II is hydrogen.

13. The process according to claim 1, wherein, during the reaction with the oxidant, a compound of the general formula III is firstly prepared:

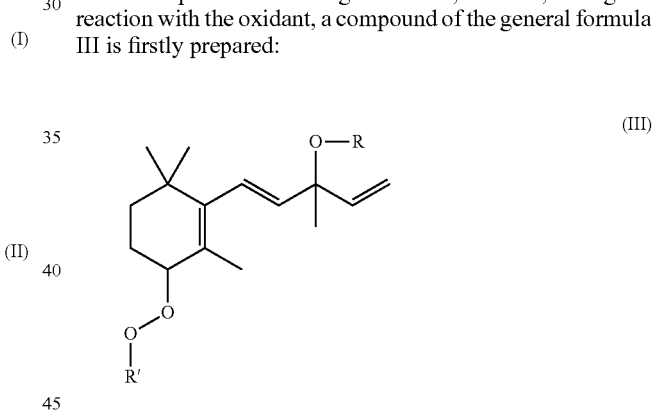

in which R is hydrogen or an OH protecting group, and R' is hydrogen or the radical derived from the organic hydroperoxide and is in particular hydrogen, alkyl or arylalkyl; and then the compound of the formula (III) is decomposed to give the compound of the formula I.

14. The process according to claim 12, wherein the compound of the formula III is decomposed thermally or by treatment with a base.

15. A process for the preparation of the phosphonium salts of the formula IV

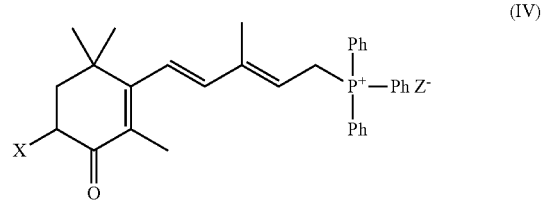

in which X is hydrogen, OH or OR", Ph is phenyl, Z⁻ is a halide anion and R" is hydrogen or an OH protecting group, which comprises the following:

i) preparing oxovinylionol or an O-protected derivative thereof of the formula I by the process according to claim 1;

ii) converting oxovinylionol or its O-protected derivative of the formula I in a manner to give a compound of the formula IV.

16. The process according to claim 15 for the preparation of a phosphonium compound of the formula IV in which X is OH, wherein step ii) comprises the following stages:

a) converting a compound of the formula I into a silyl enol ether of the formula V

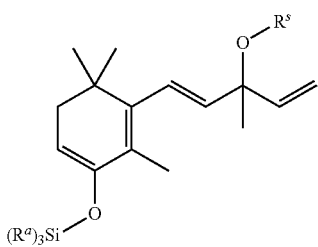

(V)

in which $R^a$ in the group $Si(R^a)_3$ can be identical or different and independently of one another are $C_1$-$C_4$-alkyl and $R^s$ is an acid-cleavable OH protecting group;

b) successively converting the compound of the formula V with a peroxocarboxylic acid and optionally subsequently hydrolyzing the resulting compound of the formula VI in which $R^a$ and $R^s$ have the abovementioned meanings, which gives a compound of the formula VII:

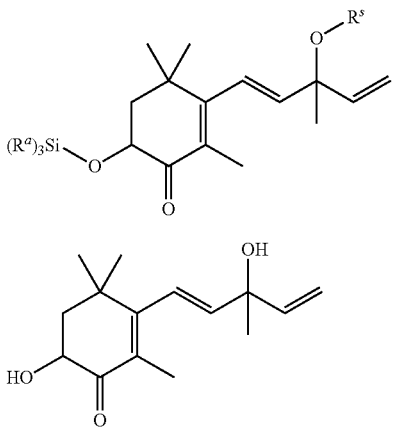

(VI)

(VII)

c) successively reacting the compound of the formula VII with a halogenating agent and subsequently with triphenylphosphane, which gives a compound of the formula IV in which X is OH, or a') converting a compound of the formula I, in which R is an acid-cleavable OH protecting group $R^s$, into its enolate, b') reacting the enolate with an N-arylsulfonyloxaziridine, which gives a compound of the formula VIa

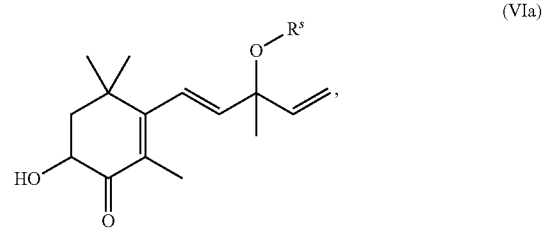

(VIa)

c) hydrolyzing the compound of the formula VIa and successively reacting the hydrolyzate with a halogenating agent and subsequently with triphenylphosphane, which gives a compound of the formula IV in which X is OH.

17. The process according to claim 15 for the preparation of a phosphonium compound of the formula IV in which X is H, wherein step ii) comprises the following stage:

c') successively reacting the compound of the formula I in which R is hydrogen with hydrogen halide HZ and subsequently with triphenylphosphane, which gives a compound of the formula IV.

18. A process for the preparation of a phosphonium salt of the formula IVa

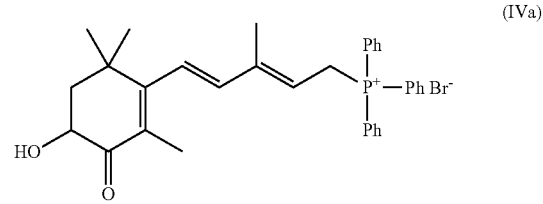

(IVa)

in which Ph is phenyl, which comprises:

a") preparing oxovinylionol or an O-protected derivative thereof of the formula I by the process according to claim 1;

converting the compound of the formula I into a silyl enol ether of the formula V

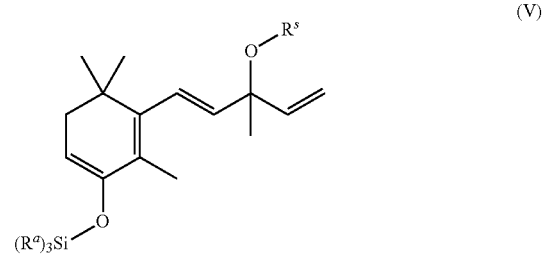

(V)

in which $R^a$ in group $Si(R^a)_3$ can be identical or different and independently of one another are $C_1$-$C_4$-alkyl and $R^s$ is an acid-cleavable OH protecting group;

b") successively reacting the compound of the formula V with a peroxo carboxylic acid and reacting the oxidation product with hydrobromic acid, which gives a compound of the formula VIa:

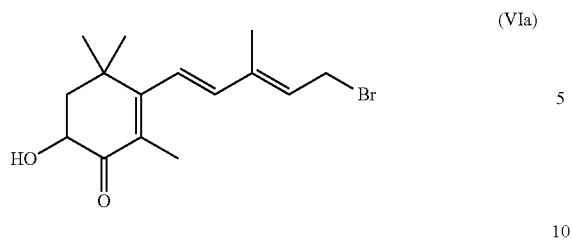
(VIa)

c') reacting the compound of the formula VIa with triphenylphosphane, which gives a compound of the formula IVa;

wherein providing the compound of the formula V comprises the following steps:

i) preparing oxovinylionol or an O-protected derivative thereof of the formula I by the process according to claim 1;

ii') converting the compound of the formula I into a silyl enol ether of the formula V.

* * * * *